US005733772A

United States Patent [19]
Williamson et al.

[11] Patent Number: 5,733,772
[45] Date of Patent: Mar. 31, 1998

[54] **CLONING AND EXPRESSION OF *PLASMODIUM FALCIPARUM* TRANSMISSION BLOCKING TARGET ANTIGEN, PFS230**

[75] Inventors: Kim C. Williamson, Rockville; David C. Kaslow, Kensington, both of Md.

[73] Assignee: The United States of America as represented by the Department of Health and Human Services, Washington, D.C.

[21] Appl. No.: 323,170

[22] Filed: Oct. 13, 1994

Related U.S. Application Data

[63] Continuation of Ser. No. 10,409, Jan. 29, 1993, abandoned.

[51] Int. Cl.$^6$ .............................. C12N 15/30; C12N 1/21; C12N 15/70
[52] U.S. Cl. ............................ 435/252.3; 435/252.33; 435/320.1; 435/69.3; 435/325; 536/23.7
[58] Field of Search ................. 536/23.7; 435/320.1, 435/252.3, 252.33, 240.1, 240.2, 255.11, 69.1, 69.3, 325; 424/185.1, 268.1; 930/210; 935/12, 65

[56] References Cited

U.S. PATENT DOCUMENTS

| | | | |
|---|---|---|---|
| 4,707,445 | 11/1987 | McCutchan et al. | 435/91 |
| 5,196,307 | 3/1993 | Earnshaw et al. | 435/7.9 |

OTHER PUBLICATIONS

Levin Science vol. 237 p. 1570 (1987).
Reeck et al. Cell vol. 50 p. 667 (1987).
Sambrook, Molecular Cloning, A Laboratory Manual, 2nd Ed. Cold Spring Harbor Laboratory, CSH, NY (1989).
Dame et al Science vol. 225 pp. 593–599 (1984).
Williamson, K. et al. (1992) "Cloning and Expression of *Plasmodium falciparum* transmission blocking target antigen Pfs230" (*Abstract of the 41st Annual Meeting of the American Society of Tropical Medicine and Hygine*) *American Journal of Tropical Medicine and Hygiene*, 47(4):94–95.
Triglia, T. et al. (1991) "Large fragments of *Plasmodium falciparum* DNA can be stable when cloned in yeast artificial chromosomes", *Chemical Abstracts*, 114(11):189.
Lewis, Alan P. (1990) "Cloning and analysis of the gene encoding the 230-kilodalton merozoite surface antigen of *Plasmodium yoelii*", *Chemical Abstracts*, 112(23):146.

Williamson, K.C., et al., "Immunoaffinity Chromatography Using Electroelution," *Biochemistry*, 296:359–362, 1992.

Elliott, J. F., et al., "Novel Gene Encoding A Large *Plasmodium falciparum* Sexual Stage Specific Antigen Cloned By Expression In Eucaryotic (COS7) Cells", *Program and Abstracts of the 40th Annual Meeting of the American Society of Tropical Medicine and Hygiene, Supplement to the American Journal of Tropical Medicine and Hygiene*, 45:270, abst.#437 (1991).

Quakyi, I. A., et al., "The 230-kDa Gamete Surface Protein of *Plasmodium falciparum* is also a Target for Transmission-Blocking Antibodies", *Journal of Immunology* 139:4213–4217 (1987).

Barr, P. J., et al., "Recombinant Pfs25 Protein of *Plasmodium falciparum* Elicits Malaria Transmission-Blocking Immunity in Experimental Animals" *Journal of Experimental Medicine* 174:1203–1208 (1991).

Good, M. F., et al., "Limited Immunological Recognition of Critical Malaria Vaccine Candiate Antigens" *Science* 242:574–577 (1988).

Wizel, B. and N. Kumar, "Identification of a Continuous and Cross-Reacting Epitope for *Plasmodium falciparum* Transmission-Blocking Immunity" *Proc. Natl. Acad. Sci.* 88:9533–9537 (1991).

Targett, G., "Immunity to Sexual Stages of Human Malaria Parasites: Immune Modulation During Natural Infections, Antigenic Determinants, and the Induction of Transmission-Blocking Immunity" *Scand. J. Infect. Dis. Suppl.* 76:79–88 (1990).

Ong, C. S. L., et al., "The Primary Antibody Response of Malaria Patients to *Plasmodium falciparum* Sexual Stage Antigens which are Potential Transmission Blocking Vaccine Candidates" *Parasite Immunology* 12:447–456 (1990).

Foo, A., et al., "Conserved and Variant Epitopes of Target Antigens of Transmission-Blocking Antibodies Among Isolates of *Plasmodium falciparum* from Malaysia" *Am. J. Trop. Med. Hyg.* 44:623–631 (1991).

*Primary Examiner*—Mary E. Mosher
*Attorney, Agent, or Firm*—Townsend and Townsend and Crew LLP

[57] ABSTRACT

Compositions comprising biologically pure Pfs230 and nucleic acids which encode them are provided. The proteins can be used induce transmission blocking immune responses in susceptible hosts.

13 Claims, 6 Drawing Sheets

CLONING AND EXPRESSION OF *PLASMODIUM FALCIPARUM* TRANSMISSION BLOCKING TARGET ANTIGEN, PFS230

This is a Continuation of application Ser. No. 08/010, 409, filed Jan. 29, 1993, now abandoned.

BACKGROUND OF THE INVENTION

Malaria continues to exact a heavy toll on humans. Between 200 million to 400 million people are infected by *Plasmodium falciparum*, the deadliest of the malarial protozoans, each year. One to four million of these people die. Approximately 25 percent of all deaths of children in rural Africa between the ages of one and four years are caused by malaria.

The life cycle of the malaria parasite is complex. Infection in man begins when young malarial parasites or sporozoites are injected into the bloodstream of a human by a mosquito. After injection the parasite localizes in liver cells. Approximately one week after injection, the parasites or merozoites are released into the bloodstream to begin the erythrocytic phase. Each parasite enters a red blood cell in order to grow and develop. When the merozoite matures in the red blood cell, it is known as a trophozoite and, when fully developed, as a schizont. A schizont is the stage when nuclear division occurs to form individual merozoites which are released to invade other red cells. After several schizogonic cycles, some parasites, instead of becoming schizonts through asexual reproduction, develop into large uninucleate parasites. These parasites undergo sexual development.

Sexual development of the malaria parasites involves the female or macrogametocyte and the male parasite or microgametocyte. These gametocytes do not undergo any further development in man. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs with the fusion of the microgamete and a macrogamete. The fertilized parasite, which is known as a zygote, then develops into an ookinete. The ookinete penetrates the midgut wall of the mosquito and develops into an oocyst, within which many small sporozoites form. When the oocyst ruptures, the sporozoites migrate to the salivary gland of the mosquito via the hemolymph. Once in the saliva of the mosquito, the parasite can be injected into a host, repeating the life cycle.

Malaria vaccines are needed against different stages in the parasite's life cycle, including the sporozoite, asexual erythrocyte, and sexual stages. Each vaccine against a particular life cycle stage increases the opportunity to control malaria in the many diverse settings in which the disease occurs. For example, sporozoite vaccines fight infection immediately after injection of the parasite into the host by the mosquito. First generation vaccines of this type have been tested in humans. Asexual erythrocytic stage vaccines are useful in reducing the severity of the disease. Multiple candidate antigens for this stage have been cloned and tested in animals and in humans.

However, as drug-resistant parasite strains render chemoprophylaxis increasingly ineffective, a great need exists for a transmission-blocking vaccine. Such a vaccine would block the portion of the parasite's life cycle that takes place in the mosquito or other arthropod vector, thus preventing even the initial infection of humans. Several surface antigens serially appear on the parasite as it develops from gametocyte to gamete to zygote to ookinete within the arthropod midgut (Rener et al., *J. Exp. Med.* 158: 976–981, 1983; Vermeulen et al., *J. Exp. Med.* 162: 1460–1476, 1985). Although some of these antigens induce transmission-blocking antibodies, their use in developing transmission blocking vaccines may be limited. For instance, the antigens may fail to generate an immune response in a broad segment of the vaccinated population. Others may only produce partial blocking of transmission.

Thus there is a need to develop transmission-blocking vaccines which induce high, long lasting antibody titers and which can be produced in large amounts at low cost. The present invention addresses these and other needs.

SUMMARY OF THE INVENTION

The present invention provides biologically pure Pfs230 polypeptides which preferably have an epitope capable of eliciting a transmission blocking immune response. The sequence of the full length protein is set forth in SEQ. ID. No. 2. The invention also provides recombinantly produced Pfs230 and isolated nucleic acids which encodes the polypeptides. The sequence of a nucleic acid which encodes the full length protein is set forth in SEQ. ID. No. 1.

Also disclosed are expression vectors comprising a promoter operably linked to a nucleic acid which encodes Pfs230 as well as cells comprising the vectors. In one embodiment, the expression vector is capable of directing expression in *E. coli*.

The invention further provides pharmaceutical compositions comprising a pharmaceutically acceptable carrier and Pfs230 in an amount sufficient to induce a transmission blocking immune response in a susceptible organism, such as a human. The Pfs230 is preferably an immunologically active fragment of the full length protein. Methods of preventing transmission of malaria comprising administering to a susceptible organism the pharmaceutical compositions are also disclosed.

DEFINITIONS

The term "Pfs230" refers to proteins expressed on the surface of *Plasmodium falciparum* gametocytes which have a molecular weight of about 360 kDa before processing. The term encompasses native proteins as well as recombinantly produced proteins that induce a transmission blocking immune response. It also includes immunologically active fragments of these proteins. "Immunologically active fragments" are those portions of the full length protein which comprise epitopes capable of eliciting a transmission blocking immune response or which are recognized by transmission blocking antibodies.

A "susceptible organism" is a Plasmodium host that is susceptible to malaria, for example, humans and chickens. The particular susceptible organism or host will depend upon the Plasmodium species.

The phrases "biologically pure" or "isolated" refer to material which is substantially or essentially free from components which normally accompany it as found in its native state. Typically, a protein is substantially pure when at least about 95% of the protein in a sample has the same amino acid sequence. Usually, protein that has been isolated to a homogenous or dominant band on a polyacrylamide gel, trace contaminants in the range of 5–10% of native protein which co-purify with the desired protein. Biologically pure material does not contain such endogenous co-purified protein.

Two sequences (either nucleic acids or polypeptides) are said to be "substantially identical" if greater than about 85% of the sequences are shared when optimally aligned and compared. Greater identity of more than about 90% is preferred, and about 95% to absolute identity is most preferred.

Another indication that nucleic sequences are substantially identical is if they hybridize to the same complementary sequence under stringent conditions. Stringent conditions will depend upon various parameters (e.g. GC content) and will be different in different circumstances. Generally, stringent conditions for nucleic acids isolated from *Plasmodium falciparum* are those in which the salt concentration is at least about 0.2 molar and the temperature is at least about 55° C.

BRIEF DESCRIPTION OF THE FIGURES

FIG. 6A is indirect immunofluorescence of intact gametes/zygotes using rPfs230/MBP-A antisera. FIG. 6B is the corresponding bright field image.

FIG. 7A is indirect immunofluorescence of intact gametes/zygotes using rPfs230/MBP-B antisera. FIG. 7B is the corresponding bright field image.

FIG. 8A is indirect immunofluorescence of intact gametes/zygotes using MBP antisera. FIG. 8B is the corresponding bright field image.

DESCRIPTION OF THE PREFERRED EMBODIMENT

Figure 1:
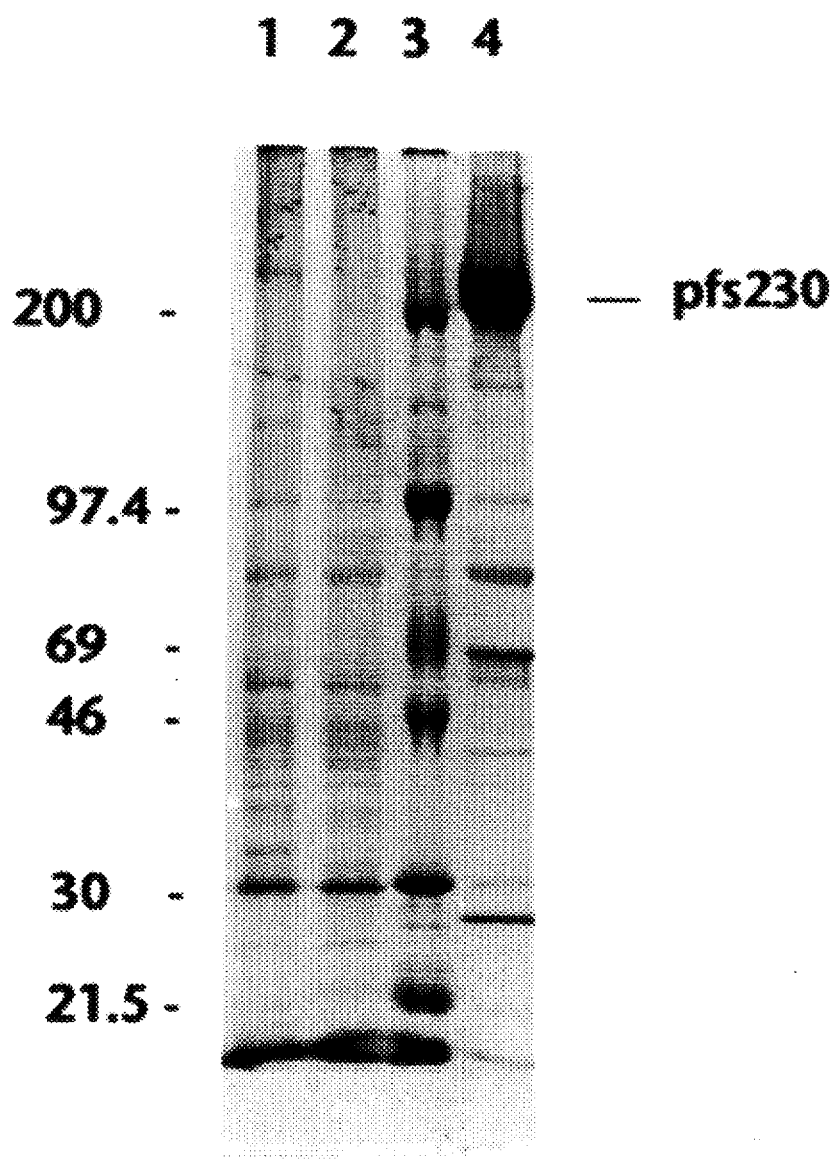
FIG. 1 shows the results of the samples from each of the purification steps which were size-fractionated on a 4–20% SDS-polyacrylamide gel and stained with coomassie blue. The lanes in the gel are as follows: Gamete\zygote extract before 1B3-Sepharose resin (lane 1), proteins that did not bind to the 1B3-Sepharose resin (lane 2), molecular weight standards (Amersham) (lane 3) and protein electroeluted from 1B3-Sepharose resin (lane 4). The molecular weight (Mr×10–3) is indicated on the left and the position of Pfs230 is indicated on the right.

The present invention provides recombinantly produced Pfs230 and fragments derived from the protein that are useful for inducing an immune response when injected into a human or other host animal. Pfs230 and homologs in other Plasmodium species can be used to block transmission of a number of parasites associated with malaria. Four species of the genus Plasmodium infect humans, *P. vivax*, *P. ovale*, *P. malariae*, and *P. falciparum*. In addition other Plasmodium species infect other animals. For instance, *P. gallinaceum* is responsible for avian malaria.

Pfs230 Protein

Pfs230 is expressed by the parasite while it undergoes gametocytogenesis in the human host. This antigen has been identified on day 2 of gametocytogenesis and continues to be produced as the gametocyte is taken up by the mosquito in a blood meal and emerges from the erythrocyte in the mosquito midgut. Once the parasite emerges from the erythrocyte, Pfs230 is exposed on the surface of the parasite, and is thus in contact with the components of the bloodmeal including antibodies and complement.

The 9.4 kb open reading frame of the nucleic acid encoding Pfs230 predicts a protein with a molecular weight of 363,243 Daltons. Pfs230 exists in at least two forms, a 360 kDa form that does not radiolabel with $^{125}$I and a $^{125}$I radiolabeled form isolated from surface labeled gametes. The labeled form when sized under reducing conditions migrates as a 310,000 molecular weight band. These results suggest that the full-length 360 kDa protein is processed to a 310 kDa protein that is expressed on the surface of the gamete.

A prior art MAb 1B3 has been reported to immunoprecipitate a 230 kDa protein from radiolabeled surface proteins of newly formed gametes and zygotes. This monoclonal antibody was reported to recognize two proteins of 260,000 and 230,000 Mr on western blots. Quakyi, et al., *J. Immunol.* 139:4213–4217 (1987), which is incorporated herein by reference. Evidence provided here shows that the protein encoded by the gene of the present invention is the same protein as that recognized by MAb 1B3. In particular, antisera raised against fusion proteins expressed from the nucleic acids of the invention recognized bands similar to those reported for Pfs230. The antisera also immunoprecipitates $^{125}$I-labeled Pfs230 and reacts with the surface of intact gametes as assayed by indirect immunofluorescence.

SEQ. ID. No. 2 is the deduced amino acid sequence of the 9.4 kB gene. The deduced amino acid sequence of Pfs230 codes for a 363 kDa polypeptide having five distinct characteristics: 1) consistent with Pfs230 being a non-integral membrane protein (Kumar & Wizel, *Mol. Biochem. Parasitol.*, 53: 113–120 (1992)), there is a presumptive signal sequence at the amino-terminus, but no other predicted hydrophobic or transmembrane regions; 2) starting at amino acid 280, there are 25 contiguous E residues; 3) beginning with amino acid 379, a four amino acid (E-E-V-G) (SEQ ID NO:3) repeat is repeated tandemly 8 times followed by 4 copies of an eight amino acid (E-E-V-G-E-E/G-E/V-G) (SEQ ID NO:4) repeat; 4) there are three regions of highly negative net charge, including amino acids 273–325, which contain the 25 E residues, amino acids 1147–1205, and amino acids 1604–1668; and 5) there are six copies of a seven cysteine motif with the consensus sequence.

The Pfs230 proteins of the invention may be recombinantly produced or may be purified from parasites isolated from infected host organisms. Methods for purifying desired proteins are well known in the art and are not presented in detail here. For a review of standard techniques see, *Methods in Enzymology*, "Guide to Protein Purification", M. Deutscher, ed. Vol. 182 (1990), which is incorporated herein by reference. For instance, Pfs230 or its homologs in other species can be purified using affinity chromatography, SDS-PAGE, and the like.

Nucleic Acids

Another aspect of the present invention relates to the cloning and recombinant expression of Pfs230 and its homologs. The recombinantly expressed polypeptides can be used in a number of ways. For instance, they can be used as transmission-blocking vaccines, as described below. The recombinantly produced proteins can also be used for raising antibodies or for T cell and B cell epitope mapping. In addition, oligonucleotides from the cloned genes can be used as probes to identify homologous polypeptides in other species. The invention relies on routine techniques in the field of recombinant genetics, well known to those of ordinary skill in the art. A basic text disclosing the general methods of use in this invention is Sambrook et al., *Molecular Cloning, A Laboratory Manual*, Cold Spring Harbor Publish., Cold Spring Harbor, N.Y. 2nd ed. (1989), which is incorporated herein by reference.

Pfs230 was immunoaffinity purified using mAb 1B3 as described in detail below. The isolated protein was then digested with trypsin. The tryptic peptides were separated by reverse phase HPLC and three well resolved peptides were microsequenced. From this amino acid sequence degenerate oligonucleotide probes were used to screen a *P. falciparum* sexual stage cDNA library.

Other methods for isolating genes encoding Pfs230 and its homologs can also be used. For instance, the amino acid sequence of the N-terminus can be determined and degenerate oligonucleotide probes, designed to hybridize to the desired gene, are synthesized. Amino acid sequencing is performed and oligonucleotide probes are synthesized according to standard techniques as described, for instance, in Sambrook et al., supra.

Oligonucleotide probes useful for identification of desired genes can also be prepared from conserved regions of related genes in other species. For instance, probes derived from a gene encoding Pfs230 may be used to screen libraries for homologous genes from other parasites of interest.

Other methods include the detection of restriction fragment length polymorphisms (RFLP) between wild type and mutant strains lacking a Pfs230 polypeptide. Amplification techniques, such as the polymerase chain reaction (PCR) can be used to amplify the desired nucleotide sequence. U.S. Pat. Nos. 4,683,195 and 4,683,202 describe this method. Sequences amplified by PCR can be purified from agarose gels and cloned into an appropriate vector according to standard techniques.

Genomic or cDNA libraries are prepared according to standard techniques as described, for instance, in Sambrook, supra. To construct genomic libraries, large segments of genomic DNA are generated by random fragmentation or restriction enzyme degradation and are ligated with vector DNA to form concatemers that can be packaged into the appropriate vector. Two kinds of vectors are commonly used for this purpose, bacteriophage lambda vectors and plasmids.

To prepare cDNA, mRNA from the parasite of interest is first isolated. Eukaryotic MRNA has at its 3' end a string of adenine nucleotide residues known as the poly-A tail. Short chains of oligo d-T nucleotides are then hybridized with the poly-A tails and serve as a primer for the enzyme, reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or phage vector for propagation in *E. coli*.

Identification of clones in either genomic or cDNA libraries harboring the desired nucleic acid segments is performed by either nucleic acid hybridization or immunological detection of the encoded protein, if an expression vector is used. The bacterial colonies are then replica plated on solid support, such as nitrocellulose filters. The cells are lysed and probed with either oligonucleotide probes described above or with antibodies to the desired protein.

Standard transfection methods are used to produce prokaryotic, mammalian, yeast or insect cell lines which express large quantities of the Pfs230 polypeptide, which is then purified using standard techniques. See, e.g., Colley et al., *J. Biol. Chem.* 264:17619–17622, 1989; and Guide to Protein Purification, supra.

The nucleotide sequences used to transfect the host cells can be modified to yield the Pfs230 polypeptide or fragments thereof, with a variety of desired properties. For example, the polypeptides can vary from the naturally-occuring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring Pfs230.

For instance, immunogenically active fragments comprising about 6 to about 300 amino acids are typically used. Shorter fragments comprising bout 100 to about 200 amino acids, preferably about 130 to about 160, may also be used. For use as vaccines, immunologically active fragments are typically preferred so long as at least one epitope capable of eliciting transmission blocking antibodies remains. Preferred polypeptide fragments of the invention include those comprising one or more of the six copies of the seven-cysteine motif noted above. Other modifications include the addition of a membrane anchoring sequence to the expressed protein. Such modifications allow the protein to be expressed on cell surfaces and thereby improve immunogenicity.

In general, modifications of the sequences encoding the homologous polypeptides may be readily accomplished by a variety of well-known techniques, such as site-directed mutagenesis (see, Gillman and Smith, *Gene* 8:81–97, 1979) and Roberts, S. et al., *Nature* 328:731–734, 1987). One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit transmission blocking can be easily determined using the mosquito feeding assays, described in Quakyi et al., supra. In addition, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

The particular procedure used to introduce the genetic material into the host cell for expression of the Pfs230 polypeptide is not particularly critical. Any of the well known procedures for introducing foreign nucleotide sequences into host cells may be used. These include the use of calcium phosphate transfection, spheroplasts, electroporation, liposomes, microinjection, plasmid vectors, viral vectors and any of the other well known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses. SV40 vectors include pSVT7 and pMT2. Vectors derived from bovine papilloma virus include pBV-1MTHA, and vectors derived from Epstein Bar virus include pHEBO, and p205. Other exemplary vectors include pRE4, pMSG, pAV009/A$^+$, pMT010/A$^+$, pMAMneo-5, bacculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, cytomegalovirus promoter, or other promoters shown effective for expression in eukaryotic cells.

The expression vector typically contains a transcription unit or expression cassette that contains all the elements required for the expression of the Pfs230 polypeptide DNA in the host cells. A typical expression cassette contains a promoter operably linked to the DNA sequence encoding a Pfs230 polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

The DNA sequence encoding the Pfs230 polypeptide will typically be linked to a cleavable signal peptide sequence to promote secretion of the encoded protein by the transformed cell. Additional elements of the cassette may include selectable markers, enhancers and, if genomic DNA is used as the structural gene, introns with functional splice donor and acceptor sites.

Enhancer elements can stimulate transcription up to 1,000 fold from linked homologous or heterologous promoters. Enhancers are active when placed downstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression*, Cold Spring Harbor Pres, Cold Spring Harbor, N.Y. 1983, which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

Efficient expression and secretion in yeast is conveniently obtained using expression vectors based on those disclosed in Barr et al., *J. Biol. Chem.* 263: 16471–16478, 1988, or U.S. Pat. No. 4,546,082, which are incorporated herein by reference. In these vectors the desired sequences are linked to sequences encoding the yeast α-factor pheromone secretory signal/leader sequence. Suitable promoters to use include the ADH2/GAPDH hybrid promoter as described in Cousens et al., *Gene* 61:265–275 (1987), which is incorporated herein by reference. Yeast cell lines suitable for the present invention include BJ 2168 (Berkeley Yeast Stock Center) as well as other commonly available lines.

Any of a number of other well known cells and cell lines can be used to express the polypeptides of the invention. For instance, prokaryotic cells such as *E. coli* can be used. Eukaryotic cells include, Chinese hamster ovary (CHO) cells, COS cells, mouse L cells, mouse A9 cells, baby hamster kidney cells, C127 cells, PC8 cells, and insect cells.

Following the growth of the recombinant cells and expression of the Pfs230 polypeptide, the culture medium is harvested for purification of the secreted protein. The media are typically clarified by centrifugation or filtration to remove cells and cell debris and the proteins are concentrated by adsorption to any suitable resin or by use of ammonium sulfate fractionation, polyethylene glycol precipitation, or by ultrafiltration. Other routine means known in the art may be equally suitable. Further purification of the Pfs230 polypeptide can be accomplished by standard techniques, for example, affinity chromatography, ion exchange chromatography, sizing chromatography, His$_6$ tagging and Ni-agarose chromatography (as described in Dobeli et al. *Mol. and Biochem. Parasit.* 41:259–268 (1990)), or other protein purification techniques to obtain homogeneity. The purified proteins are then used to produce pharmaceutical compositions, as described below.

Transmission-blocking Antibodies

A further aspect of the invention includes antibodies against Pfs230 or its homologous polypeptides. The antibodies are useful for blocking transmission of parasites. Thus, antibodies can be used as therapeutic agents to block transmission.

The multitude of techniques available to those skilled in the art for production and manipulation of various immunoglobulin molecules can be readily applied to block transmission. As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. Immunoglobulins may exist in a variety of forms besides antibodies, including for example, Fv, Fab, and F(ab)$_2$, as well as in single chains. For a general review of immunoglobulin structure and function see, *Fundamental Immunology*, 2d Ed., W. E. Paul ed., Ravens Press, New York, (1989) which is incorporated herein by reference.

Monoclonal antibodies which bind Pfs230 can be produced by a variety of means. The production of non-human monoclonal antibodies, e.g., murine, lagomorpha, equine, etc., is well known and may be accomplished by, for example, immunizing the animal with a preparation containing Pfs230. Antibody-producing cells obtained from the immunized animals are immortalized and screened, or screened first for the production antibodies which bind Pfs230 and then immortalized. For a discussion of general procedures of monoclonal antibody production see Harlow and Lane, *Antibodies, A Laboratory Manual* Cold Spring Harbor Publications, New York (1988), which is incorporated herein by reference.

It may be desirable to transfer the antigen binding regions of the non-human antibodies, e.g., the F(ab')$_2$ or hypervariable regions, to human constant regions (Fc) or framework regions by recombinant DNA techniques to produce substantially human molecules. Such methods are generally known in the art and are described in, for example, U.S. Pat. No. 4,816,397, EP publications 173,494 and 239,400, which are incorporated herein by reference. Alternatively, one may isolate DNA sequences which encode a human monoclonal antibody or portions thereof that specifically bind to Pfs230 by screening a DNA library from human B cells according to the general protocol outlined by Huse et al., *Science* 246:1275-1281 (1989), incorporated herein by reference, and then cloning and amplifying the sequences which encode the antibody (or binding fragment) of the desired specificity.

Vaccines

The Pfs230 polypeptides of the present invention are also useful as prophylactics, or vaccines, for blocking transmission of malaria or other diseases caused by parasites. Compositions containing the polypeptides are administered to a subject, giving rise to an anti-Pfs230 polypeptide immune response. The Pfs230 polypeptide-specific antibodies then block transmission of the parasite from the subject to the arthropod vector, preventing the parasite from completing its life cycle. An amount of prophylactic composition sufficient to result in blocking of transmission is defined to be an "immunologically effective dose."

The isolated nucleic acid sequence coding for Pfs230 or its homologous polypeptides can also be used to transform viruses which transfect host cells in the susceptible organism. Live attenuated viruses, such as vaccinia or adenovirus, are convenient alternatives for vaccines because they are inexpensive to produce and are easily transported and administered. Vaccinia vectors and methods useful in immunization protocols are described in, e.g., U.S. Pat. No. 4,722,848, incorporated herein by reference.

Suitable viruses for use in the present invention include, but are not limited to, pox viruses, such as, canarypox and cowpox viruses, and vaccinia viruses, alpha viruses, adenoviruses, and other animal viruses. The recombinant viruses can be produced by methods well known in the art: for example, using homologous recombination or ligating two plasmids together. A recombinant canarypox or cowpox virus can be made, for example, by inserting the gene encoding the Pfs230, immunologically active segment of Pfs230 or other homologous polypeptide into a plasmid so that it is flanked with viral sequences on both sides. The gene is then inserted into the virus genome through homologous recombination.

The recombinant virus of the present invention can be used to induce anti-Pfs230 polypeptide antibodies in mammals, such as mice or humans. In addition, the recombinant virus can be used to produce the Pfs230 polypeptides by infecting host cells which in turn express the polypeptide.

The present invention also relates to host cells infected with the recombinant virus of the present invention. The host cells of the present invention are preferably eukaryotic, such as yeast cells, or mammalian, such as BSC-1 cells. Host cells infected with the recombinant virus express the Pfs230 polypeptides on their cell surfaces. In addition, membrane extracts of the infected cells induce transmission blocking antibodies when used to inoculate or boost previously inoculated mammals.

In the case of vaccinia virus (for example, strain WR), the sequence encoding the Pfs230 polypeptides can be inserted into the viral genome by a number of methods including homologous recombination using a transfer vector, pTKgpt-OFIS as described in Kaslow et al., *Science* 252:1310-1313, 1991, which is incorporated herein by reference.

The Pfs230 polypeptides, or recombinant viruses of the present invention can be used in pharmaceutical and vaccine compositions that are useful for administration to mammals, particularly humans, to block transmission of a variety of infectious diseases. The compositions are suitable for single administrations or a series of administrations. When given as a series, inoculations subsequent to the initial administration are given to boost the immune response and are typically referred to as booster inoculations. Suitable formulations are found in *Remington's Pharmaceutical Sciences*, Mack Publishing Company, Philadelphia, Pa., 17th ed. (1985), which is incorporated herein by reference.

The pharmaceutical compositions of the invention are intended for parenteral or oral administration. Preferably, the pharmaceutical compositions are administered parenterally, e.g., subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

In therapeutic applications, Pfs230 polypeptides or viruses of the invention are administered to a patient in an amount sufficient to prevent parasite development in the arthropod and thus block transmission of the disease. An amount adequate to accomplish this is defined as a "therapeutically effective dose." Amounts effective for this use will depend on, e.g., the particular polypeptide or virus, the manner of administration, the weight and general state of health of the patient, and the judgment of the prescribing physician.

The vaccines of the invention contain as an active ingredient an immunogenically effective amount of the Pfs230 polypeptides or recombinant virus as described herein. Useful carriers are well known in the art, and include, e.g., thyroglobulin, albumins such as human serum albumin, tetanus toxoid, polyamino acids such as poly(D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. In addition, the compositions can be administered in slow release particles as described in Langer, Science 249:1527-1533 (1990).

Vaccine compositions containing the polypeptides or viruses of the invention are administered to a patient to elicit a transmission-blocking immune response against the antigen and thus prevent spread of the disease through the arthropod vector. Such an amount is defined as an "immunogenically effective dose." In this use, the precise amounts again depend on the patient's state of health and weight, the mode of administration, and the nature of the formulation, but generally range for the initial immunization (that is for therapeutic or prophylactic administration) from about 1.0 µg to about 1 mg of peptide for a 70 kg patient, followed by boosting dosages of from about 1.0 µg to about 100 µg of peptide pursuant to a boosting regimen over weeks to months.

The following examples are offered by way of illustration, not by way of limitation.

EXAMPLE 1
Isolation of Pfs230

Pfs230 was immunoaffinity purified using monoclonal 1B3 (mAb 1B3) (Quakyi, et al., J. Immunol., 139:4213-4217 (1987)). It was electroeluted from mAb 1B3-resin prepared as described in Williamson, et al., Anal. Biochem., 206:359-362 (1992), reduced and alkylated, run in one lane of a 4% gel and then transferred electrophoretically to nitrocellulose. The band corresponding to Pfs230 was excised then digested in situ with trypsin. The tryptic peptides were separated by reverse phase HPLC and three well resolved peptides were microsequenced. From this amino acid sequence degenerate oligonucleotide probes were designed utilizing P. falciparum codon bias and used to screen a P. falciparum sexual stage cDNA library prepared according to standard techniques.

FIG. 1 shows the results of the samples from each of the purification steps which were size-fractionated on a 4-20% SDS-polyacrylamide gel and stained with coomassie blue. The lanes in gel are as follows: Gamete/zygote extract before 1B3-Sepharose resin (lane 1), proteins that did not bind to the 1B3-Sepharose resin (lane 2), molecular weight standards (Amersham) (lane 3) and protein electroeluted from 1B3-Sepharose resin (lane 4). The molecular weight ($Mr \times 10^3$) is indicated on the left and the position of Pfs230 is indicated on the right.

Oligonucleotide probes from each of the three tryptic peptides hybridized to a 4.4 kB insert of an isolated clone. Sequencing revealed open reading frames at both the 5' and 3' ends of the 4.4 kB clone, therefore synthetic oligonucleotides probes corresponding to the ends were used to rescreen the library and obtain overlapping clones that extend the sequence. This process was continued until cDNA clones covering the entire 9.4 kB open reading frame were isolated. The deduced amino acid sequence of the 9.4 kB gene (SEQ. ID. No. 2) contains all 3 tryptic peptides that were microsequenced.

Figure 2:
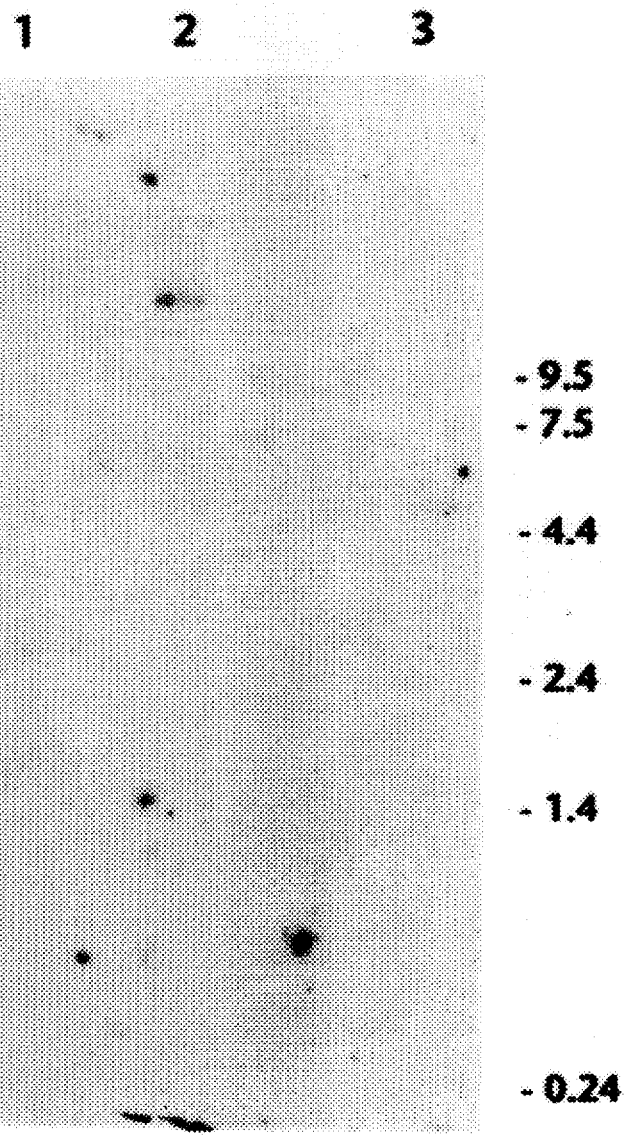
FIG. 2 shows Northern analysis of *P. falciparum* RNA from various stages in the life cycle. Lane 1 comprises RNA from an asexual stage, lane 2 is RNA from gametocytes (stage 2 & 3), and lane 3 is RNA from zygotes/gametes (5 hours post emergence). The blot was probed with the random-primer labeled 4.4 kb insert.

The Pfs230 RNA transcript is 12.5 kB and sexual stage-specific as shown in the Northern analysis of P. falciparum RNA in FIG. 2. Equal amounts of RNA were run in each lane (1) asexual, (2) gametocytes (stage 2 & 3), and (3) zygotes/gametes (5 hours post emergence). The blot was probed with the random-prime labeled 4.4 kb insert described above. The message is most abundant in gametocytes. With a long exposure of the northern a faint band can be seen in RNA from 5 hour zygotes but there is no band with asexual RNA. Oligonucleotide probes from the extreme 5' and 3' ends of the ORF hybridize to what appears to be the same transcript.

The 9.4 kB open reading frame predicts a protein with a molecular weight of 363,243 kDa, this is larger than the 260,000 and 230,000 Mr reported for the proteins mAb 1B3 recognizes by western blot. Only the 230,000 band was shown to be radiolabeled when live gametes were surface-labeled with $^{125}I$. Since mAb 1B3 does not react with reduced Pfs230 it has been difficult to obtain an accurate molecular weight of the protein. Quakyi, et al., supra.

Figure 3:
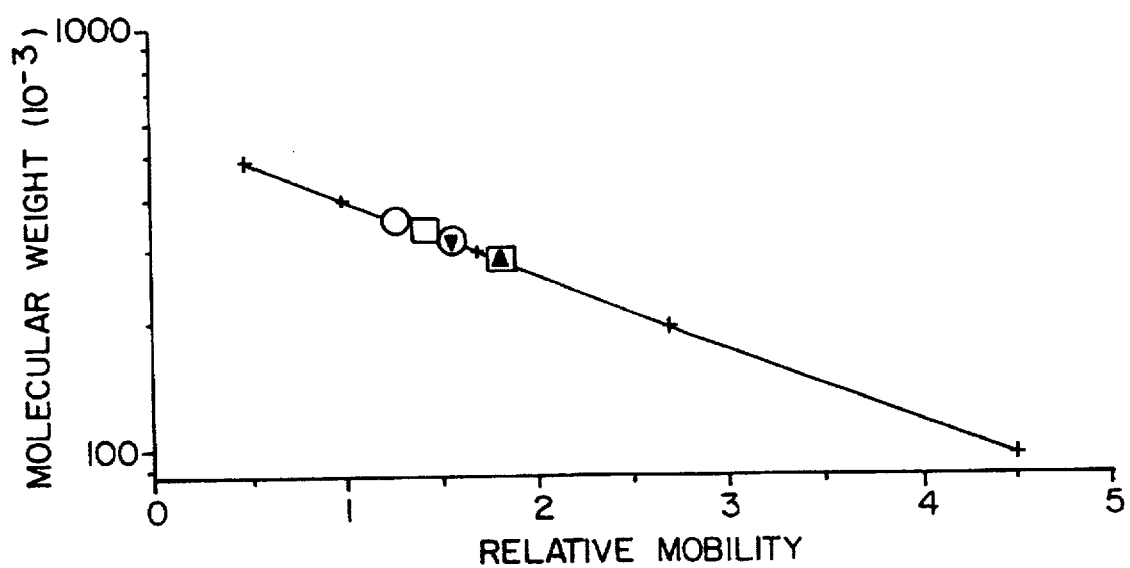
FIG. 3 shows molecular weight determination of Pfs230. Proteins from $^{125}$I-surface-labeled gametes were size-fractionated on a 4% polyacrylamide gel under nonreducing (□, ▲) and reducing (○, ▼) conditions, then transferred to nitrocellulose and immunoblotted with a 1:500 dilution of rPfs230/MBP-A antisera. The relative mobility of molecular weight markets (+), $^{125}$I-labeled Pfs230 (▲, ▼) and rPfs230/MBP-A immunoreactive bands (□, ○) was plotted.

Prior art estimates of the size of the protein have been made with molecular weight standards having molecular weights less than 200 kDa. To more accurately determine the molecular weight, radiolabeled Pfs230 from surface labeled gametes was carefully sized under reducing conditions using molecular weight markers ranging from 100,000 to 500,000. Reduced $^{125}I$ labeled Pfs230 migrated as a 310,000 molecular weight band (FIG. 3).

Figure 4A:
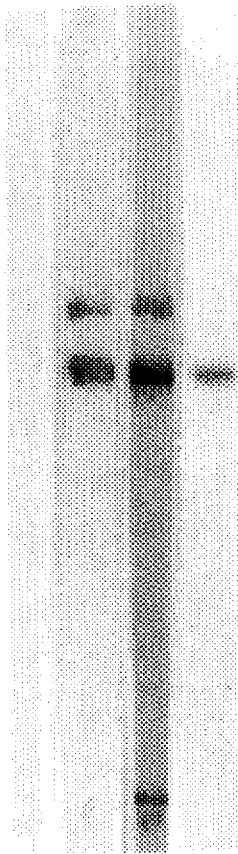
FIGS. 4A and 4B show Western blots of Triton X-100 extracted $^{125}$I-surface-labeled gametes/zygotes size-fractionated on a 4% polyacrylamide gel under (A) nonreducing or (B) reducing conditions and reacted with a 1:5,000 dilution of MBP antisera (lane 1), rPfs230/MBP-A antisera (lane 2), and rPfs230/MBP-B antisera (lane 3). Also shown is an autoradiograph of the rPfs230/MBP-B lane (lane 4). The $M_r$ standards (×10$^{-3}$) are indicated.
Figure 4B:
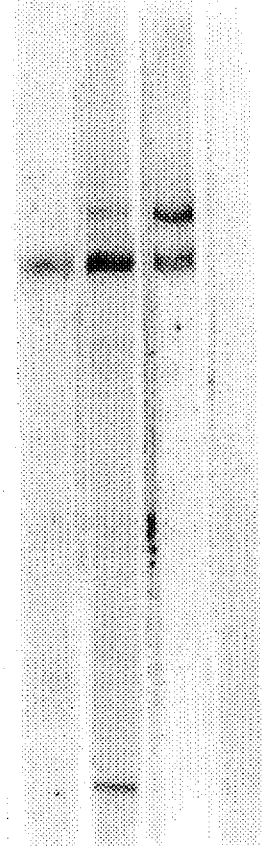

To confirm that the cloned gene was indeed Pfs230, antibodies to a 2.0-2.2 kB section of the gene expressed in E. coli as fusions with maltose-binding protein (rPfs230/MBP-A E-B, described below) were used to assay a western blot of Triton X-100 extracted P. falciparum gametes/zygotes. FIGS. 4A and 4B show Western blots of Triton X-100 extracted $^{125}I$-surface-labeled gametes reacted with a 1:5,000 dilution of MPB antisera (lane 1), rPfs230/MBP-A antisera (lane 2), and rPfs230/MBP-B antisera (lane 3). Also shown is an autoradiograph of rPfs230/MBP-B (lane 4).

When the extract was size-fractionated under nonreducing conditions the rPfs230/MBP-A and -B antisera recognized bands of 325,000 kDa and 275,000 kDa, and under reducing conditions bands of 360,000 kDa and 310,000 kDa (FIGS. 4A and 4B, respectively. Neither preimmune sera nor antisera to MBP alone reacted with any specific bands.

The lower bands, under both reducing and nonreducing conditions comigrated with $^{125}I$ labeled Pfs230 (FIGS. 4A and 4B). This suggests that only the lower band was exposed on the surface of the gamete. Possibly, the 360,000 protein is processed to a 310,000 form as it is moved to the surface of the gamete.

Figure 5:
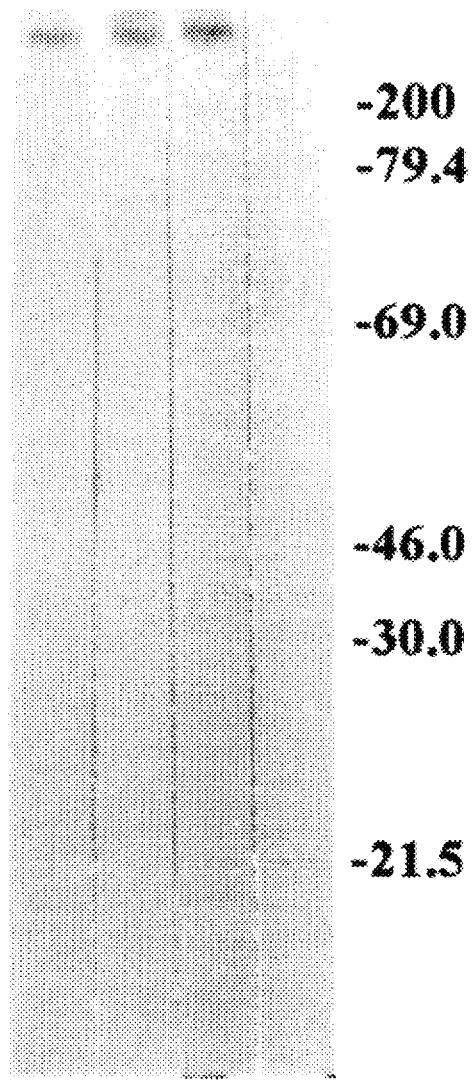
FIG. 5 shows immunoprecipitation of radiolabeled Pfs230 from a Triton X-100 extract of $^{125}$I-surface-labeled gametes/zygotes. mAb 1B3 (lane 1), rPfs230/MBP-A antisera (lane 2), rPfs230/MBP-B antisera (lane 3) and MBP antisera (lane 4) were incubated with extract, then precipitated with protein A-sepharose. The precipitated material was size-fractionated on a 4–20% polyacrylamide gel and the radiolabeled bands were visualized by autoradiography.

To determine whether the rPfs230/MBP antisera recognized the native (nondenatured) surface form of Pfs230, the antisera was used to immunoprecipitate radiolabeled Pfs230 from a Triton X-100 extract of surface-labeled *P. falciparum* gametes/zygotes (FIG. 5). Proteins immunoprecipitated by the following antibodies or antisera were loaded on the gel: mAb 1B3 (lane 1), rPfs230/MBP A antisera (lane 2), rPfs230/MBP-B (lane 3) and MBP antisera (lane 4). The antibodies and antisera were incubated with a Triton X-100 extract of $^{125}$-I surface labeled gametes and precipitated with protein A-sepharose as described above. The precipitated material was run out on a 4–20% acrylamide gel. The radiolabeled bands were visualized by autoradiography. FIG. 5 shows that $^{125}$I-labeled Pfs230 was precipitated by rPfs230/MBP 1B antisera and monoclonal 1B3 but not MBP antisera.

Figure 6A:
FIGS. 6A and 6B show indirect immunofluorescence assay of intact gametes/zygotes.
Figure 6B:
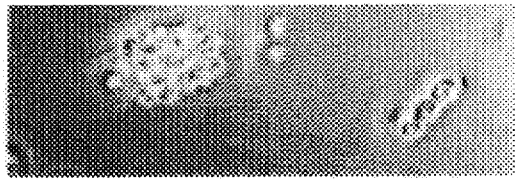
Figure 7A:
FIGS. 7A and 7B show indirect immunofluorescence assay of intact gametes/zygotes.
Figure 7B:
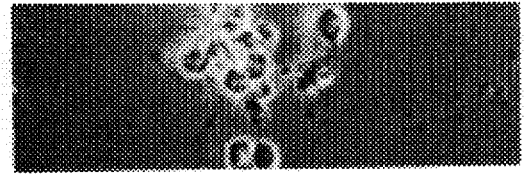
Figure 8A:
FIGS. 8A and 8B show indirect immunofluorescence assay of intact gametes/zygotes.
Figure 8B:
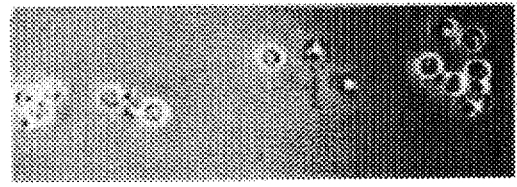

Finally, an indirect immunofluorescence assay of intact gametes/zygotes was used to show that rPfs230/MBP-A and B antisera recognized the surface of live gametes/zygotes (FIGS. 6A and 7A). FIGS. 6B and 7B, respectively, are the corresponding bright field image. FIG. 8A shows the results of the same experiment with MBP antisera. FIG. 8B is the corresponding bright field image.

Expression of the Gene in *E. coli*

Pfs230 open reading frame was PCR-amplified using a sense primer with a 5' Sma I site encoding amino acids 439–444 for rPfs230/MBP-A or amino acids 2398–2405 for rPfs230/MBP-B, and an antisense primer with a 3' stop codon followed by a Sal I site encoding amino acid 1127–1135 for rPfs230/MBP-A or nucleotides 9607–9624 in the 3' untranslated region for rPfs230/MBP-B. Gel-purified PCR products were ligated into Stu I/Sma I cut PIH-902 expression vector (gift of Paul Riggs, New England Biolabs). IPTG-induced rPfs230-maltose binding protein fusion was purified from an extract of *E. coli* (DH10B strain, BRL) on amylose resin and use to immumize NIH outbred mice according to the method of Rawlings, et al., *J. Biol. Chem.*, 267: 3976–3982 (1992).

Although the present invention has been described in some detail by way of illustration and example for purposes of clarity and understanding, it will be apparent that certain changes and modifications may be practiced within the scope of the appended claims.

What is claimed is:

1. An isolated nucleic acid which encodes a full length PFS230 polypeptide, wherein:
 the polypeptide has a molecular weight, before processing, of about 360 kDa as measured on a reducing gel;
 the polypeptide has a molecular weight, after processing, of about 310 kDa as measured on a reducing gel; and,
 a subsequence of the nucleic acid can be amplified in a PCR reaction using a sense primer corresponding to a nucleic acid subsequence of SEQ ID NO:1 which encodes amino acids 439–444 of SEQ ID NO:2 and an antisense primer complementary to a nucleic acid subsequence of SEQ ID No:1 which encodes amino acids 1127–1135 of SEQ ID NO:2.

2. The nucleic acid of claim 1 which encodes the polypeptide of SEQ ID No. 2.

3. The nucleic acid of claim 1 which has the nucleic acid sequence of SEQ ID No.1.

4. A composition comprising an isolated nucleic acid encoding the polypeptide of SEQ. ID. NO.2.

5. The composition of claim 4, wherein the nucleic acid has a sequence as set forth in SEQ. ID. No. 1.

6. An expression vector comprising a promoter operably linked to a nucleic acid encoding a polypeptide which comprises an amino acid subsequence selected from the group consisting of amino acids 2398 to 3135 as set forth in SEQ ID No. 2, and amino acids 439 to 1135 as set forth in SEQ ID No. 2.

7. The expression vector of claim 6, wherein the nucleic acid encodes a full-length PFS230 as set forth in Seq. ID. No. 2.

8. The expression vector of claim 7, wherein the nucleic acid has the sequence set forth in Seq. ID. No. 1.

9. The expression vector of claim 6, wherein the nucleic acid comprises a sequence as set forth in SEQ. ID. No. 1.

10. The expression vector of claim 6, wherein the nucleic acid encodes a polypeptide which consists of amino acids 439 to 1135 as set forth in SEQ ID No. 2, or amino acids 2398 to 3135 as set forth in SEQ ID No. 2.

11. A composition comprising a cell comprising the vector of claim 6.

12. The composition of claim 11, wherein the cell is *E. coli*.

13. The composition of claim 12, wherein the vector is PIH-902.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 9636 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 149..9556

( x i ) SEQUENCE DESCRIPTION: SEQ ID NO:1:

```
TATTTTTTTT ATTTTTTTA TTTTTTATT TTTTATTAT TTTTATTTTT TTATTTTTTT      60

TATTTTTTTA TTTTATATT TTTATATTT TTTCTTCTA CCATTCTTTT ATCCTTCTTG     120

ATCGTATATT TTTCTTTTCT TTTAATAA ATG AAG AAA ATT ATA ACG CTG AAG     172
                                 Met Lys Lys Ile Ile Thr Leu Lys
                                  1               5

AAT CTA TTC CTC ATT ATC CTG GTA TAC ATA TTT AGC GAG AAA AAA GAC    220
Asn Leu Phe Leu Ile Ile Leu Val Tyr Ile Phe Ser Glu Lys Lys Asp
     10              15                  20

CTG CGT TGT AAT GTG ATA AAG GGA AAT AAT ATT AAG GAT GAT GAA GAT    268
Leu Arg Cys Asn Val Ile Lys Gly Asn Asn Ile Lys Asp Asp Glu Asp
 25              30                  35                      40

AAG AGA TTC CAC TTA TTT TAT TAT TCC CAC AAC CTT TTT AAG ACA CCC    316
Lys Arg Phe His Leu Phe Tyr Tyr Ser His Asn Leu Phe Lys Thr Pro
                 45                  50                  55

GAA ACA AAA GAA AAG AAG AAT AAA AAG GAG TGC TTT TAT AAA AAT GGT    364
Glu Thr Lys Glu Lys Lys Asn Lys Lys Glu Cys Phe Tyr Lys Asn Gly
             60                  65                  70

GGT ATT TAT AAT TTA TCT AAA GAA ATA AGG ATG AGA AAG GAT ACA TCC    412
Gly Ile Tyr Asn Leu Ser Lys Glu Ile Arg Met Arg Lys Asp Thr Ser
         75                  80                  85

GTA AAA ATA AAA CAA AGA ACA TGT CCC TTT CAT AAA GAA GGA AGT TCA    460
```

| | | | | | | | | | | | | | | | | |
|---|---|---|---|---|---|---|---|---|---|---|---|---|---|---|---|---|
| Val | Lys 90 | Ile | Lys | Gln | Arg | Thr 95 | Cys | Pro | Phe | His | Lys 100 | Glu | Gly | Ser | Ser | |
| TTT | GAA | ATG | GGT | TCA | AAG | AAT | ATT | ACA | TGT | TTT | TAT | CCT | ATC | GTA | GGG | 508 |
| Phe 105 | Glu | Met | Gly | Ser | Lys 110 | Asn | Ile | Thr | Cys | Phe 115 | Tyr | Pro | Ile | Val | Gly 120 | |
| AAG | AAG | GAA | AGG | AAA | ACA | CTG | GAC | ACA | ATT | ATT | ATA | AAA | AAG | AAT | GTA | 556 |
| Lys | Lys | Glu | Arg | Lys 125 | Thr | Leu | Asp | Thr | Ile 130 | Ile | Ile | Lys | Lys | Asn 135 | Val | |
| ACA | AAT | GAT | CAT | GTT | GTT | AGT | AGT | GAT | ATG | CAT | TCC | AAT | GTA | CAA | GAA | 604 |
| Thr | Asn | Asp | His 140 | Val | Val | Ser | Ser | Asp 145 | Met | His | Ser | Asn | Val 150 | Gln | Glu | |
| AAA | AAT | ATG | ATA | TTA | ATA | AGA | AAT | ATA | GAT | AAA | GAA | AAT | AAA | AAT | GAT | 652 |
| Lys | Asn | Met 155 | Ile | Leu | Ile | Arg | Asn 160 | Ile | Asp | Lys | Glu | Asn 165 | Lys | Asn | Asp | |
| ATA | CAA | AAT | GTT | GAG | GAA | AAA | ATA | CAA | AGG | GAT | ACA | TAC | GAA | AAT | AAA | 700 |
| Ile | Gln | Asn 170 | Val | Glu | Glu | Lys | Ile 175 | Gln | Arg | Asp | Thr | Tyr 180 | Glu | Asn | Lys | |
| GAT | TAT | GAA | AGT | GAT | GAT | ACA | CTT | ATA | GAA | TGG | TTT | GAT | GAT | AAT | ACA | 748 |
| Asp 185 | Tyr | Glu | Ser | Asp | Asp 190 | Thr | Leu | Ile | Glu | Trp 195 | Phe | Asp | Asp | Asn | Thr 200 | |
| AAT | GAA | GAA | AAC | TTT | TTA | CTA | ACT | TTT | TTA | AAA | AGG | TGC | TTG | ATG | AAA | 796 |
| Asn | Glu | Glu | Asn | Phe 205 | Leu | Leu | Thr | Phe | Leu 210 | Lys | Arg | Cys | Leu | Met 215 | Lys | |
| ATA | TTT | TCT | TCA | CCC | AAA | AGA | AAA | AAA | ACT | GTA | GTA | CAA | AAA | AAA | CAT | 844 |
| Ile | Phe | Ser | Ser 220 | Pro | Lys | Arg | Lys | Lys 225 | Thr | Val | Val | Gln | Lys 230 | Lys | His | |
| AAG | TCT | AAT | TTT | TTT | ATA | AAC | AGT | TCG | TTG | AAA | TAT | ATA | TAT | ATG | TAT | 892 |
| Lys | Ser | Asn 235 | Phe | Phe | Ile | Asn | Ser 240 | Ser | Leu | Lys | Tyr | Ile 245 | Tyr | Met | Tyr | |
| TTA | ACC | CCC | TCG | GAT | AGC | TTT | AAC | CTA | GTA | CGT | CGA | AAC | AGA | AAT | TTG | 940 |
| Leu | Thr | Pro 250 | Ser | Asp | Ser | Phe | Asn 255 | Leu | Val | Arg | Arg | Asn 260 | Arg | Asn | Leu | |
| GAT | GAG | GAA | GAC | ATG | TCG | CCC | AGG | GAT | AAT | TTT | GTA | ATA | GAT | GAT | GAG | 988 |
| Asp 265 | Glu | Glu | Asp | Met | Ser 270 | Pro | Arg | Asp | Asn | Phe 275 | Val | Ile | Asp | Asp | Glu 280 | |
| GAA | GAA | GAG | GAG | GAG | GAA | GAA | GAA | GAG | GAA | GAG | GAA | GAA | GAG | GAA | GAA | 1036 |
| Glu | Glu | Glu | Glu | Glu 285 | Glu | Glu | Glu | Glu | Glu 290 | Glu | Glu | Glu | Glu | Glu 295 | Glu | |
| GAA | GAA | GAA | GAG | GAG | GAG | GAA | GAA | TAT | GAT | GAT | TAT | GTT | TAT | GAA | GAA | 1084 |
| Glu | Glu | Glu | Glu | Glu 300 | Glu | Glu | Glu | Tyr | Asp 305 | Asp | Tyr | Val | Tyr 310 | Glu | Glu | |
| AGT | GGG | GAT | GAA | ACA | GAA | GAA | CAA | TTA | CAA | GAG | GAA | CAT | CAG | GAA | GAA | 1132 |
| Ser | Gly | Asp 315 | Glu | Thr | Glu | Glu | Gln 320 | Leu | Gln | Glu | Glu | His 325 | Gln | Glu | Glu | |
| GTA | GGT | GCT | GAA | TCT | TCA | GAA | GAA | AGT | TTT | AAT | GAT | GAG | GAT | GAA | GAT | 1180 |
| Val | Gly 330 | Ala | Glu | Ser | Ser | Glu 335 | Glu | Ser | Phe | Asn | Asp 340 | Glu | Asp | Glu | Asp | |
| TCT | GTA | GAA | GCA | CGG | GAT | GGA | GAT | ATG | ATA | AGA | GTT | GAC | GAA | TAT | TAT | 1228 |
| Ser 345 | Val | Glu | Ala | Arg | Asp 350 | Gly | Asp | Met | Ile | Arg 355 | Val | Asp | Glu | Tyr | Tyr 360 | |
| GAA | GAC | CAA | GAT | GGT | GAT | ACT | TAT | GAT | AGT | ACA | ATA | AAA | AAT | GAA | GAT | 1276 |
| Glu | Asp | Gln | Asp | Gly 365 | Asp | Thr | Tyr | Asp | Ser 370 | Thr | Ile | Lys | Asn | Glu 375 | Asp | |
| GTA | GAT | GAA | GAG | GTA | GGT | GAA | GAG | GTA | GGT | GAA | GAG | GTA | GGT | GAA | GAG | 1324 |
| Val | Asp | Glu | Glu 380 | Val | Gly | Glu | Glu | Val 385 | Gly | Glu | Glu | Val | Gly 390 | Glu | Glu | |
| GTA | GGT | GAA | GAG | GTA | GGT | GAA | GAG | GTA | GGT | GAA | GAG | GTA | GGT | GAA | GAG | 1372 |
| Val | Gly | Glu 395 | Glu | Val | Gly | Glu | Glu 400 | Val | Gly | Glu | Glu | Val 405 | Gly | Glu | Glu | |
| GTA | GGT | GAA | GAG | GTA | GGT | GAA | GAA | GAA | GGT | GAA | GAG | GTA | GGT | GAA | GGG | 1420 |

-continued

| | | | | | | | | | | | | | | | |
|---|---|---|---|---|---|---|---|---|---|---|---|---|---|---|---|
| Val | Gly | Glu | Glu | Val | Gly | Glu | Glu | Glu | Gly | Glu | Glu | Val | Gly | Glu | Gly |
| | 410 | | | | 415 | | | | | 420 | | | | | |

| GTA | GGT | GAA | GAG | GTA | GGT | GAA | GAA | GAA | GGT | GAA | GAG | GTA | GGT | GAA | GAA | 1468 |
|---|---|---|---|---|---|---|---|---|---|---|---|---|---|---|---|---|
| Val | Gly | Glu | Glu | Val | Gly | Glu | Glu | Glu | Gly | Glu | Glu | Val | Gly | Glu | Glu | |
| 425 | | | | | 430 | | | | | 435 | | | | | 440 | |

| GAA | GGT | GAA | TAT | GTA | GAT | GAA | AAA | GAA | AGG | CAA | GGT | GAA | ATA | TAT | CCA | 1516 |
|---|---|---|---|---|---|---|---|---|---|---|---|---|---|---|---|---|
| Glu | Gly | Glu | Tyr | Val | Asp | Glu | Lys | Glu | Arg | Gln | Gly | Glu | Ile | Tyr | Pro | |
| | | | | 445 | | | | | 450 | | | | | 455 | | |

| TTT | GGT | GAT | GAA | GAA | GAA | AAA | GAT | GAA | GGT | GGA | GAA | AGT | TTT | ACC | TAT | 1564 |
|---|---|---|---|---|---|---|---|---|---|---|---|---|---|---|---|---|
| Phe | Gly | Asp | Glu | Glu | Glu | Lys | Asp | Glu | Gly | Gly | Glu | Ser | Phe | Thr | Tyr | |
| | | | 460 | | | | | 465 | | | | | 470 | | | |

| GAA | AAG | AGC | GAG | GTT | GAT | AAA | ACA | GAT | TTG | TTT | AAA | TTT | ATA | GAA | GGG | 1612 |
|---|---|---|---|---|---|---|---|---|---|---|---|---|---|---|---|---|
| Glu | Lys | Ser | Glu | Val | Asp | Lys | Thr | Asp | Leu | Phe | Lys | Phe | Ile | Glu | Gly | |
| | | 475 | | | | | 480 | | | | | 485 | | | | |

| GGT | GAA | GGA | GAT | GAT | GTA | TAT | AAA | GTG | GAT | GGT | TCC | AAA | GTT | TTA | TTA | 1660 |
|---|---|---|---|---|---|---|---|---|---|---|---|---|---|---|---|---|
| Gly | Glu | Gly | Asp | Asp | Val | Tyr | Lys | Val | Asp | Gly | Ser | Lys | Val | Leu | Leu | |
| | 490 | | | | | 495 | | | | | 500 | | | | | |

| GAT | GAT | GAT | ACA | ATT | AGT | AGA | GTA | TCT | AAA | AAA | CAT | ACT | GCA | CGA | GAT | 1708 |
|---|---|---|---|---|---|---|---|---|---|---|---|---|---|---|---|---|
| Asp | Asp | Asp | Thr | Ile | Ser | Arg | Val | Ser | Lys | Lys | His | Thr | Ala | Arg | Asp | |
| 505 | | | | | 510 | | | | | 515 | | | | | 520 | |

| GGT | GAA | TAT | GGT | GAA | TAT | GGT | GAA | GCT | GTC | GAA | GAT | GGA | GAA | AAT | GTT | 1756 |
|---|---|---|---|---|---|---|---|---|---|---|---|---|---|---|---|---|
| Gly | Glu | Tyr | Gly | Glu | Tyr | Gly | Glu | Ala | Val | Glu | Asp | Gly | Glu | Asn | Val | |
| | | | | 525 | | | | | 530 | | | | | 535 | | |

| ATA | AAA | ATA | ATT | AGA | AGT | GTG | TTA | CAA | AGT | GGT | GCA | TTA | CCA | AGT | GTA | 1804 |
|---|---|---|---|---|---|---|---|---|---|---|---|---|---|---|---|---|
| Ile | Lys | Ile | Ile | Arg | Ser | Val | Leu | Gln | Ser | Gly | Ala | Leu | Pro | Ser | Val | |
| | | | 540 | | | | | 545 | | | | | 550 | | | |

| GGT | GTT | GAT | GAG | TTA | GAT | AAA | ATC | GAT | TTG | TCA | TAT | GAA | ACA | ACA | GAA | 1852 |
|---|---|---|---|---|---|---|---|---|---|---|---|---|---|---|---|---|
| Gly | Val | Asp | Glu | Leu | Asp | Lys | Ile | Asp | Leu | Ser | Tyr | Glu | Thr | Thr | Glu | |
| | | 555 | | | | | 560 | | | | | 565 | | | | |

| AGT | GGA | GAT | ACT | GCT | GTA | TCC | GAA | GAT | TCA | TAT | GAT | AAA | TAT | GCA | TCT | 1900 |
|---|---|---|---|---|---|---|---|---|---|---|---|---|---|---|---|---|
| Ser | Gly | Asp | Thr | Ala | Val | Ser | Glu | Asp | Ser | Tyr | Asp | Lys | Tyr | Ala | Ser | |
| | 570 | | | | | 575 | | | | | 580 | | | | | |

| AAT | AAT | ACA | AAT | AAA | GAA | TAC | GTT | TGT | GAT | TTT | ACA | GAT | CAA | TTA | AAA | 1948 |
|---|---|---|---|---|---|---|---|---|---|---|---|---|---|---|---|---|
| Asn | Asn | Thr | Asn | Lys | Glu | Tyr | Val | Cys | Asp | Phe | Thr | Asp | Gln | Leu | Lys | |
| 585 | | | | | 590 | | | | | 595 | | | | | 600 | |

| CCA | ACA | GAA | AGT | GGT | CCT | AAA | GTA | AAA | AAA | TGT | GAA | GTA | AAA | GTT | AAT | 1996 |
|---|---|---|---|---|---|---|---|---|---|---|---|---|---|---|---|---|
| Pro | Thr | Glu | Ser | Gly | Pro | Lys | Val | Lys | Lys | Cys | Glu | Val | Lys | Val | Asn | |
| | | | | 605 | | | | | 610 | | | | | 615 | | |

| GAG | CCA | TTA | ATA | AAA | GTA | AAA | ATA | ATA | TGT | CCA | TTA | AAA | GGT | TCT | GTA | 2044 |
|---|---|---|---|---|---|---|---|---|---|---|---|---|---|---|---|---|
| Glu | Pro | Leu | Ile | Lys | Val | Lys | Ile | Ile | Cys | Pro | Leu | Lys | Gly | Ser | Val | |
| | | | 620 | | | | | 625 | | | | | 630 | | | |

| GAA | AAA | TTA | TAT | GAT | AAT | ATA | GAA | TAT | GTA | CCT | AAA | AAA | AGC | CCA | TAT | 2092 |
|---|---|---|---|---|---|---|---|---|---|---|---|---|---|---|---|---|
| Glu | Lys | Leu | Tyr | Asp | Asn | Ile | Glu | Tyr | Val | Pro | Lys | Lys | Ser | Pro | Tyr | |
| | | 635 | | | | | 640 | | | | | 645 | | | | |

| GTT | GTT | TTA | ACA | AAA | GAG | GAA | ACT | AAA | CTA | AAG | GAA | AAA | CTT | CTC | TCG | 2140 |
|---|---|---|---|---|---|---|---|---|---|---|---|---|---|---|---|---|
| Val | Val | Leu | Thr | Lys | Glu | Glu | Thr | Lys | Leu | Lys | Glu | Lys | Leu | Leu | Ser | |
| | 650 | | | | | 655 | | | | | 660 | | | | | |

| AAA | CTT | ATT | TAT | GGT | TTA | TTA | ATA | TCT | CCG | ACG | GTT | AAC | GAA | AAG | GAG | 2188 |
|---|---|---|---|---|---|---|---|---|---|---|---|---|---|---|---|---|
| Lys | Leu | Ile | Tyr | Gly | Leu | Leu | Ile | Ser | Pro | Thr | Val | Asn | Glu | Lys | Glu | |
| 665 | | | | | 670 | | | | | 675 | | | | | 680 | |

| AAT | AAT | TTT | AAA | GAA | GGT | GTT | ATT | GAA | TTT | ACT | CTT | CCC | CCT | GTG | GTA | 2236 |
|---|---|---|---|---|---|---|---|---|---|---|---|---|---|---|---|---|
| Asn | Asn | Phe | Lys | Glu | Gly | Val | Ile | Glu | Phe | Thr | Leu | Pro | Pro | Val | Val | |
| | | | | 685 | | | | | 690 | | | | | 695 | | |

| CAC | AAG | GCA | ACA | GTG | TTT | TAT | TTT | ATA | TGT | GAT | AAT | TCA | AAA | ACA | GAA | 2284 |
|---|---|---|---|---|---|---|---|---|---|---|---|---|---|---|---|---|
| His | Lys | Ala | Thr | Val | Phe | Tyr | Phe | Ile | Cys | Asp | Asn | Ser | Lys | Thr | Glu | |
| | | | 700 | | | | | 705 | | | | | 710 | | | |

| GAT | GAT | AAC | AAA | AAA | GGA | AAT | AGA | GGG | ATT | GTA | GAA | GTG | TAT | GTA | GAA | 2332 |
|---|---|---|---|---|---|---|---|---|---|---|---|---|---|---|---|---|
| Asp | Asp | Asn | Lys | Lys | Gly | Asn | Arg | Gly | Ile | Val | Glu | Val | Tyr | Val | Glu | |
| | | 715 | | | | | 720 | | | | | 725 | | | | |

| CCA | TAT | GGT | AAT | AAA | ATT | AAT | GGA | TGT | GCT | TTC | TTG | GAT | GAA | GAT | GAA | 2380 |

| | | | | | | | | | | | | | | | | |
|---|---|---|---|---|---|---|---|---|---|---|---|---|---|---|---|---|
| Pro | Tyr 730 | Gly | Asn | Lys | Ile 735 | Asn | Gly | Cys | Ala | Phe 740 | Leu | Asp | Glu | Asp | Glu | |
| GAA Glu 745 | GAA Glu | GAA Lys | AAA Tyr | TAT Gly 750 | GGT Asn | AAT Gln | CAA Ile | ATT Glu | GAA Glu 755 | GAA Asp | GAT Glu | GAA His | CAT Asn | AAT Glu 760 | GAG | 2428 |
| AAG Lys | ATA Ile | AAA Lys | ATG Met 765 | AAA Thr | ACA Phe | TTC Phe | TTT Thr | ACC Gln 770 | CAG Asn | AAT Ile | ATA Tyr | TAT Lys | AAA Lys 775 | AAA Asn | AAT | 2476 |
| AAT Asn | ATA Ile | TAT Tyr | CCA Pro 780 | TGT Cys | TAT Tyr | ATG Met | AAA Lys | TTA Leu 785 | TAT Tyr | AGC Ser | GGA Gly | GAT Asp | ATA Ile 790 | GGT Gly | GGT Gly | 2524 |
| ATT Ile | CTA Leu | TTT Phe 795 | CCT Pro | AAG Lys | AAT Asn | ATA Ile | AAA Lys 800 | TCA Ser | ACA Thr | ACG Thr | TGT Cys | TTT Phe 805 | GAA Glu | GAG Glu | ATG Met | 2572 |
| ATA Ile | CCT Pro 810 | TAT Tyr | AAT Asn | AAA Lys | GAA Glu | ATA Ile 815 | AAA Lys | TGG Trp | AAT Asn | AAA Lys 820 | GAA Glu | AAT Asn | AAA Lys | AGT Ser | TTA Leu | 2620 |
| GGT Gly 825 | AAC Asn | TTA Leu | GTT Val | AAT Asn | AAT Asn 830 | TCT Ser | GTA Val | GTA Val | TAT Tyr | AAT Asn 835 | AAA Lys | GAG Glu | ATG Met | AAT Asn | GCA Ala 840 | 2668 |
| AAA Lys | TAT Tyr | TTT Phe | AAT Asn | GTT Val 845 | CAG Gln | TAT Tyr | GTT Val | CAC His | ATT Ile 850 | CCT Pro | ACA Thr | AGT Ser | TAT Tyr | AAA Lys 855 | GAT Asp | 2716 |
| ACA Thr | TTA Leu | AAT Asn | TTA Leu 860 | TTT Phe | TGT Cys | AGT Ser | ATT Ile | ATA Ile 865 | TTA Leu | AAA Lys | GAA Glu | GAG Glu | GAA Ser 870 | AGT | AAT Asn | 2764 |
| TTA Leu | ATT Ile | TCT Ser 875 | ACT Thr | TCT Ser | TAT Tyr | TTA Leu | GTA Val 880 | TAT Tyr | GTA Val | AGT Ser | ATT Ile | AAT Asn 885 | GAA Glu | GAA Glu | TTA Leu | 2812 |
| AAT Asn | TTT Phe 890 | TCA Ser | CTT Leu | TTC Phe | GAT Asp | TTT Tyr 895 | TAT Glu | GAA Ser | TCA Phe | TTT Val | GTA Pro 900 | CCT Ile | ATA Lys | AAA Lys | AAA | 2860 |
| ACC Thr 905 | ATA Ile | CAA Gln | GTA Val | GCT Ala | CAA Gln 910 | AAG Lys | AAT Asn | GTA Val | AAT Asn | AAT Asn 915 | AAA Lys | GAA Glu | CAT His | GAT Asp | TAT Tyr 920 | 2908 |
| ACA Thr | TGT Cys | GAT Asp | TTT Phe | ACC Thr 925 | GAT Asp | AAA Lys | TTA Leu | GAT Asp | AAA Lys 930 | ACG Thr | GTT Val | CCT Pro | TCT Ser | ACT Thr 935 | GCT Ala | 2956 |
| AAT Asn | GGG Gly | AAG Lys | AAA Lys 940 | TTA Leu | TTT Phe | ATA Ile | TGT Cys | AGA Arg 945 | AAG Lys | CAT His | TTA Leu | AAA Lys | GAA Glu 950 | TTT Phe | GAT Asp | 3004 |
| ACA Thr | TTT Phe | ACC Thr 955 | TTA Leu | AAA Lys | TGT Cys | AAT Asn | GTT Val 960 | AAT Asn | AAA Lys | ACA Thr | CAA Gln | TAT Tyr 965 | CCA Pro | AAT Asn | ATC Ile | 3052 |
| GAG Glu | ATA Ile 970 | TTT Phe | CCT Pro | AAA Lys | ACA Thr | TTA Leu 975 | AAA Lys | GAT Asp | AAA Lys | AAG Lys | GAA Glu 980 | GTA Val | TTA Leu | AAA Lys | TTA Leu | 3100 |
| GAT Asp 985 | CTT Leu | GAT Asp | ATA Ile | CAA Gln | TAT Tyr 990 | CAA Gln | ATG Met | TTT Phe | AGT Ser | AAA Lys 995 | TTT Phe | TTT Phe | AAA Lys | TTC Phe | AAT Asn 1000 | 3148 |
| ACA Thr | CAG Gln | AAT Asn | GCA Ala | AAG Lys 1005 | TAT Tyr | TTA Leu | AAT Asn | TTA Leu | TAT Tyr 1010 | CCA Pro | TAT Tyr | TAT Tyr | TTA Leu | ATT Ile 1015 | TTT Phe | 3196 |
| CCA Pro | TTT Phe | AAT Asn | CAT His | ATA Ile 1020 | GGA Gly | AAA Lys | AAA Lys | GAA Glu | TTA Leu 1025 | AAA Lys | AAT Asn | AAT Asn | CCT Pro | ACA Thr 1030 | TAT Tyr | 3244 |
| AAA Lys | AAT Asn | CAT His | AAA Lys 1035 | GAT Asp | GTG Val | AAA Lys | TAT Tyr | TTT Phe 1040 | GAG Glu | CAA Gln | TCA Ser | TCT Ser | GTA Val 1045 | TTA Leu | TCT Ser | 3292 |
| CCC Pro | TTA Leu | TCT Ser | TCC Ser | GCA Ala | GAC Asp | AGT Ser | TTA Leu | GGG Gly | AAA Lys | TTA Leu | TTA Leu | AAT Asn | TTT Phe | TTA Leu | GAT Asp | 3340 |

```
                Pro Leu Ser Ser Ala Asp Ser Leu Gly Lys Leu Leu Asn Phe Leu Asp
                    1050                1055                1060

ACT CAA GAG ACG GTA TGT CTT ACG GAA AAG ATA AGA TAT TTA AAT TTA          3388
Thr Gln Glu Thr Val Cys Leu Thr Glu Lys Ile Arg Tyr Leu Asn Leu
1065                1070                1075                1080

AGT ATC AAT GAG TTA GGA TCT GAT AAT AAT ACA TTT TCT GTA ACA TTT          3436
Ser Ile Asn Glu Leu Gly Ser Asp Asn Asn Thr Phe Ser Val Thr Phe
                    1085                1090                1095

CAG GTT CCA CCA TAT ATA GAT ATT AAG GAA CCT TTT TAT TTT ATG TTT          3484
Gln Val Pro Pro Tyr Ile Asp Ile Lys Glu Pro Phe Tyr Phe Met Phe
                1100                1105                1110

GGT TGT AAT AAT AAT AAA GGT GAA GGG AAT ATC GGA ATT GTT GAA TTA          3532
Gly Cys Asn Asn Asn Lys Gly Glu Gly Asn Ile Gly Ile Val Glu Leu
            1115                1120                1125

TTA ATA TCT AAG CAA GAA GAA AAG ATT AAA GGA TGT AAT TTC CAT GAA          3580
Leu Ile Ser Lys Gln Glu Glu Lys Ile Lys Gly Cys Asn Phe His Glu
        1130                1135                1140

TCT AAA TTA GAT TAT TTC AAT GAA AAC ATT TCT AGT GAT ACA CAT GAA          3628
Ser Lys Leu Asp Tyr Phe Asn Glu Asn Ile Ser Ser Asp Thr His Glu
1145                1150                1155                1160

TGT ACA TTG CAT GCA TAT GAA AAT GAT ATA ATT GGA TTT AAT TGT TTA          3676
Cys Thr Leu His Ala Tyr Glu Asn Asp Ile Ile Gly Phe Asn Cys Leu
                1165                1170                1175

GAA ACT ACT CAT CCT AAT GAG GTT GAG GTT GAA GTT GAA GAT GCT GAA          3724
Glu Thr Thr His Pro Asn Glu Val Glu Val Glu Val Glu Asp Ala Glu
                    1180                1185                1190

ATA TAT CTT CAA CCT GAG AAT TGT TTT AAT AAT GTA TAT AAA GGA TTG          3772
Ile Tyr Leu Gln Pro Glu Asn Cys Phe Asn Asn Val Tyr Lys Gly Leu
                1195                1200                1205

AAT TCT GTT GAT ATT ACT ACT ATA TTA AAA AAT GCA CAA ACA TAT AAT          3820
Asn Ser Val Asp Ile Thr Thr Ile Leu Lys Asn Ala Gln Thr Tyr Asn
            1210                1215                1220

ATA AAT AAT AAG AAA ACA CCT ACC TTT TTA AAA ATT CCA CCA TAT AAT          3868
Ile Asn Asn Lys Lys Thr Pro Thr Phe Leu Lys Ile Pro Pro Tyr Asn
1225                1230                1235                1240

TTA TTA GAA GAT GTC GAA ATT AGT TGC CAA TGT ACT ATT AAA CAA GTT          3916
Leu Leu Glu Asp Val Glu Ile Ser Cys Gln Cys Thr Ile Lys Gln Val
                1245                1250                1255

GTT AAA AAA ATA AAA GTT ATT ATA ACC AAA AAT GAT ACA GTA TTA TTA          3964
Val Lys Lys Ile Lys Val Ile Ile Thr Lys Asn Asp Thr Val Leu Leu
                    1260                1265                1270

AAA AGA GAA GTG CAA TCT GAG TCT ACA TTA GAT GAT AAA ATA TAT AAA          4012
Lys Arg Glu Val Gln Ser Glu Ser Thr Leu Asp Asp Lys Ile Tyr Lys
                1275                1280                1285

TGT GAA CAT GAA AAT TTT ATT AAT CCA AGA GTA AAT AAA ACA TTT GAT          4060
Cys Glu His Glu Asn Phe Ile Asn Pro Arg Val Asn Lys Thr Phe Asp
            1290                1295                1300

GAA AAT GTA GAA TAT ACA TGT AAT ATA AAA ATA GAG AAT TTC TTT AAT          4108
Glu Asn Val Glu Tyr Thr Cys Asn Ile Lys Ile Glu Asn Phe Phe Asn
1305                1310                1315                1320

TAT ATT CAA ATA TTT TGT CCA GCC AAA GAT CTT GGT ATT TAT AAA AAT          4156
Tyr Ile Gln Ile Phe Cys Pro Ala Lys Asp Leu Gly Ile Tyr Lys Asn
                1325                1330                1335

ATA CAA ATG TAT TAT GAT ATT GTA AAA CCA ACA AGA GTA CCA CAA TTT          4204
Ile Gln Met Tyr Tyr Asp Ile Val Lys Pro Thr Arg Val Pro Gln Phe
                    1340                1345                1350

AAA AAA TTT AAT AAT GAA GAA TTA CAT AAA TTA ATT CCT AAT TCA GAA          4252
Lys Lys Phe Asn Asn Glu Glu Leu His Lys Leu Ile Pro Asn Ser Glu
                1355                1360                1365

ATG TTA CAT AAA ACA AAA GAA ATG TTA ATT TTA TAT AAT GAA GAA AAA          4300
```

```
         Met Leu His Lys Thr Lys Glu Met Leu Ile Leu Tyr Asn Glu Glu Lys
             1370            1375            1380

GTG GAT CTA TTA CAT TTT TAT GTA TTC TTA CCA ATA TAT ATA AAA GAC         4348
Val Asp Leu Leu His Phe Tyr Val Phe Leu Pro Ile Tyr Ile Lys Asp
1385            1390            1395            1400

ATA TAT GAA TTC AAT ATA GTA TGT GAT AAT TCA AAA ACA ATG TGG AAA         4396
Ile Tyr Glu Phe Asn Ile Val Cys Asp Asn Ser Lys Thr Met Trp Lys
                1405            1410            1415

AAT CAA TTA GGA GGA AAA GTT ATA TAT CAT ATT ACT GTT TCA AAA AGA         4444
Asn Gln Leu Gly Gly Lys Val Ile Tyr His Ile Thr Val Ser Lys Arg
1420            1425            1430

GAG CAG AAA GTA AAA GGT TGT TCA TTT GAT AAT GAA CAT GCA CAT ATG         4492
Glu Gln Lys Val Lys Gly Cys Ser Phe Asp Asn Glu His Ala His Met
            1435            1440            1445

TTT AGT TAT AAT AAA ACT AAT GTA AAA AAT TGT ATT ATA GAT GCT AAA         4540
Phe Ser Tyr Asn Lys Thr Asn Val Lys Asn Cys Ile Ile Asp Ala Lys
        1450            1455            1460

CCT AAA GAT TTG ATA GGT TTC GTT TGT CCC TCT GGT ACC TTA AAA TTA         4588
Pro Lys Asp Leu Ile Gly Phe Val Cys Pro Ser Gly Thr Leu Lys Leu
1465            1470            1475            1480

ACA AAT TGT TTT AAA GAT GCA ATA GTA CAT ACA AAT TTA ACA AAT ATT         4636
Thr Asn Cys Phe Lys Asp Ala Ile Val His Thr Asn Leu Thr Asn Ile
                1485            1490            1495

AAT GGT ATA CTT TAT TTA AAA AAT AAT TTG GCT AAC TTT ACA TAT AAA         4684
Asn Gly Ile Leu Tyr Leu Lys Asn Asn Leu Ala Asn Phe Thr Tyr Lys
            1500            1505            1510

CAT CAA TTT AAT TAT ATG GAA ATA CCA GCT TTA ATG GAT AAT GAT ATA         4732
His Gln Phe Asn Tyr Met Glu Ile Pro Ala Leu Met Asp Asn Asp Ile
        1515            1520            1525

TCA TTT AAA TGT ATA TGT GTT GAT TTA AAA AAA AAA AAA TAT AAT GTC         4780
Ser Phe Lys Cys Ile Cys Val Asp Leu Lys Lys Lys Lys Tyr Asn Val
1530            1535            1540

AAA TCA CCA TTA GGA CCT AAA GTT TTA CGT GCT CTT TAT AAA AAA TTA         4828
Lys Ser Pro Leu Gly Pro Lys Val Leu Arg Ala Leu Tyr Lys Lys Leu
                1545            1550            1555            1560

AAT ATA AAA TTT GAT AAT TAT GTT ACT GGC ACT GAT CAA AAT AAA TAT         4876
Asn Ile Lys Phe Asp Asn Tyr Val Thr Gly Thr Asp Gln Asn Lys Tyr
            1565            1570            1575

CTT ATG ACA TAT ATG GAT TTA CAT TTA TCT CAT AAA CGT AAT TAT TTA         4924
Leu Met Thr Tyr Met Asp Leu His Leu Ser His Lys Arg Asn Tyr Leu
        1580            1585            1590

AAG GAA TTA TTT CAT GAT TTA GGT AAA AAA AAA CCA GCA GAT ACA GAT         4972
Lys Glu Leu Phe His Asp Leu Gly Lys Lys Lys Pro Ala Asp Thr Asp
1595            1600            1605

GCT AAC CCT GAA TCT ATT ATC GAA TCT TTA AGT ATT AAT GAA TCT AAT         5020
Ala Asn Pro Glu Ser Ile Ile Glu Ser Leu Ser Ile Asn Glu Ser Asn
        1610            1615            1620

GAA TCT GGA CCT TTT CCA ACC GGG GAT GTA GAT GCA GAA CAT TTA ATA         5068
Glu Ser Gly Pro Phe Pro Thr Gly Asp Val Asp Ala Glu His Leu Ile
1625            1630            1635            1640

TTA GAA GGA TAT GAT ACA TGG GAA AGT TTA TAT GAT GAA CAA TTA GAA         5116
Leu Glu Gly Tyr Asp Thr Trp Glu Ser Leu Tyr Asp Glu Gln Leu Glu
                1645            1650            1655

GAA GTT ATA TAT AAT GAT ATT GAA TCT TTA GAA TTA AAA GAT ATT GAA         5164
Glu Val Ile Tyr Asn Asp Ile Glu Ser Leu Glu Leu Lys Asp Ile Glu
            1660            1665            1670

CAA TAT GTT TTA CAA GTT AAT TTA AAA GCT CCA AAA TTA ATG ATG TCT         5212
Gln Tyr Val Leu Gln Val Asn Leu Lys Ala Pro Lys Leu Met Met Ser
        1675            1680            1685

GCT CAA ATT CAT AAT AAT AGA CAT GTA TGT GAT TTC TCA AAA AAT AAT         5260
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ala | Gln | Ile | His | Asn | Asn | Arg | His | Val | Cys | Asp | Phe | Ser | Lys | Asn | Asn |      |
|     | 1690|     |     |     | 1695|     |     |     |     | 1700|     |     |     |     |     |      |
| TTA | ATT | GTA | CCA | GAA | TCA | TTA | AAA | AAA | AAA | GAA | GAG | CTT | GGT | GGT | AAT | 5308 |
| Leu | Ile | Val | Pro | Glu | Ser | Leu | Lys | Lys | Lys | Glu | Glu | Leu | Gly | Gly | Asn |      |
| 1705|     |     |     |     | 1710|     |     |     |     | 1715|     |     |     |     | 1720|      |
| CCA | GTA | AAT | ATT | CAT | TGT | TAT | GCA | TTA | TTA | AAA | CCT | TTA | GAT | ACA | TTA | 5356 |
| Pro | Val | Asn | Ile | His | Cys | Tyr | Ala | Leu | Leu | Lys | Pro | Leu | Asp | Thr | Leu |      |
|     |     |     |     | 1725|     |     |     |     | 1730|     |     |     |     | 1735|     |      |
| TAT | GTA | AAA | TGT | CCT | ACA | TCA | AAA | GAT | AAT | TAT | GAA | GCT | GCT | AAA | GTA | 5404 |
| Tyr | Val | Lys | Cys | Pro | Thr | Ser | Lys | Asp | Asn | Tyr | Glu | Ala | Ala | Lys | Val |      |
|     |     |     | 1740|     |     |     |     | 1745|     |     |     |     | 1750|     |     |      |
| AAC | ATA | TCT | GAA | AAC | GAC | AAT | GAA | TAT | GAG | TTA | CAA | GTT | ATA | TCA | TTA | 5452 |
| Asn | Ile | Ser | Glu | Asn | Asp | Asn | Glu | Tyr | Glu | Leu | Gln | Val | Ile | Ser | Leu |      |
|     |     | 1755|     |     |     |     | 1760|     |     |     |     | 1765|     |     |     |      |
| ATC | GAA | AAA | AGA | TTT | CAT | AAT | TTT | GAG | ACG | TTA | GAA | TCG | AAG | AAA | CCT | 5500 |
| Ile | Glu | Lys | Arg | Phe | His | Asn | Phe | Glu | Thr | Leu | Glu | Ser | Lys | Lys | Pro |      |
|     | 1770|     |     |     |     | 1775|     |     |     |     | 1780|     |     |     |     |      |
| GGA | AAT | GGA | GAT | GTA | GTA | GTA | CAT | AAT | GGT | GTT | GTA | GAT | ACT | GGA | CCT | 5548 |
| Gly | Asn | Gly | Asp | Val | Val | Val | His | Asn | Gly | Val | Val | Asp | Thr | Gly | Pro |      |
| 1785|     |     |     |     | 1790|     |     |     |     | 1795|     |     |     |     | 1800|      |
| GTA | TTA | GAT | AAC | AGT | ACA | TTT | GAA | AAA | TAT | TTT | AAA | AAT | ATA | AAA | ATA | 5596 |
| Val | Leu | Asp | Asn | Ser | Thr | Phe | Glu | Lys | Tyr | Phe | Lys | Asn | Ile | Lys | Ile |      |
|     |     |     |     | 1805|     |     |     |     | 1810|     |     |     |     | 1815|     |      |
| AAA | CCA | GAT | AAA | TTT | TTT | GAG | AAA | GTT | ATA | AAT | GAA | TAT | GAT | GAT | ACT | 5644 |
| Lys | Pro | Asp | Lys | Phe | Phe | Glu | Lys | Val | Ile | Asn | Glu | Tyr | Asp | Asp | Thr |      |
|     |     |     | 1820|     |     |     |     | 1825|     |     |     |     | 1830|     |     |      |
| GAA | GAA | GAA | AAA | GAT | TTA | GAA | AGT | ATA | TTA | CCT | GGG | GCT | ATT | GTT | AGT | 5692 |
| Glu | Glu | Glu | Lys | Asp | Leu | Glu | Ser | Ile | Leu | Pro | Gly | Ala | Ile | Val | Ser |      |
|     |     | 1835|     |     |     |     | 1840|     |     |     |     | 1845|     |     |     |      |
| CCT | ATG | AAA | GTT | TTA | AAA | AAA | AAG | GAT | CCT | TTT | ACA | TCA | TAT | GCT | GCT | 5740 |
| Pro | Met | Lys | Val | Leu | Lys | Lys | Lys | Asp | Pro | Phe | Thr | Ser | Tyr | Ala | Ala |      |
|     | 1850|     |     |     |     | 1855|     |     |     |     | 1860|     |     |     |     |      |
| TTT | GTT | GTT | CCA | CCA | ATT | GTT | CCC | AAA | GAT | TTA | CAT | TTT | AAA | GTA | GAA | 5788 |
| Phe | Val | Val | Pro | Pro | Ile | Val | Pro | Lys | Asp | Leu | His | Phe | Lys | Val | Glu |      |
| 1865|     |     |     |     | 1870|     |     |     |     | 1875|     |     |     |     | 1880|      |
| TGT | AAT | AAT | ACA | GAA | TAT | AAA | GAT | GAA | AAT | CAA | TAT | ATA | AGT | GGA | TAT | 5836 |
| Cys | Asn | Asn | Thr | Glu | Tyr | Lys | Asp | Glu | Asn | Gln | Tyr | Ile | Ser | Gly | Tyr |      |
|     |     |     |     | 1885|     |     |     |     | 1890|     |     |     |     | 1895|     |      |
| AAT | GGT | ATA | ATA | CAT | ATT | GAT | ATA | TCA | AAT | AGT | AAT | AGG | AAA | ATT | AAT | 5884 |
| Asn | Gly | Ile | Ile | His | Ile | Asp | Ile | Ser | Asn | Ser | Asn | Arg | Lys | Ile | Asn |      |
|     |     |     | 1900|     |     |     |     | 1905|     |     |     |     | 1910|     |     |      |
| GGA | TGT | GAT | TTC | TCT | ACG | AAC | AAT | AGT | TCT | ATT | TTA | ACA | TCC | AGT | GTA | 5932 |
| Gly | Cys | Asp | Phe | Ser | Thr | Asn | Asn | Ser | Ser | Ile | Leu | Thr | Ser | Ser | Val |      |
|     |     | 1915|     |     |     |     | 1920|     |     |     |     | 1925|     |     |     |      |
| AAA | TTA | GTA | AAT | GGA | GAA | ACT | AAA | AAT | TGT | GAA | ATA | AAT | ATA | AAT | AAT | 5980 |
| Lys | Leu | Val | Asn | Gly | Glu | Thr | Lys | Asn | Cys | Glu | Ile | Asn | Ile | Asn | Asn |      |
| 1930|     |     |     |     | 1935|     |     |     |     | 1940|     |     |     |     |     |      |
| AAT | GAA | GTA | TTT | GGT | ATC | ATA | TGT | GAT | AAT | GAA | ACA | AAT | TTA | GAT | CCA | 6028 |
| Asn | Glu | Val | Phe | Gly | Ile | Ile | Cys | Asp | Asn | Glu | Thr | Asn | Leu | Asp | Pro |      |
| 1945|     |     |     |     | 1950|     |     |     |     | 1955|     |     |     |     | 1960|      |
| GAA | AAA | TGT | TTT | CAT | GAA | ATA | TAT | AGT | AAA | GAT | AAT | AAA | ACT | GTA | AAA | 6076 |
| Glu | Lys | Cys | Phe | His | Glu | Ile | Tyr | Ser | Lys | Asp | Asn | Lys | Thr | Val | Lys |      |
|     |     |     |     | 1965|     |     |     |     | 1970|     |     |     |     | 1975|     |      |
| AAA | TTT | CGT | GAA | GTT | ATA | CCT | AAT | ATA | GAT | ATA | TTC | TCA | TTA | CAT | AAT | 6124 |
| Lys | Phe | Arg | Glu | Val | Ile | Pro | Asn | Ile | Asp | Ile | Phe | Ser | Leu | His | Asn |      |
|     |     |     | 1980|     |     |     |     | 1985|     |     |     |     | 1990|     |     |      |
| TCT | AAT | AAG | AAA | AAA | GTT | GCA | TAT | GCT | AAA | GTA | CCT | TTA | GAT | TAT | ATT | 6172 |
| Ser | Asn | Lys | Lys | Lys | Val | Ala | Tyr | Ala | Lys | Val | Pro | Leu | Asp | Tyr | Ile |      |
|     |     | 1995|     |     |     |     | 2000|     |     |     |     | 2005|     |     |     |      |
| AAT | AAA | TTA | TTA | TTT | TCT | TGT | TCA | TGT | AAA | ACA | TCA | CAT | ACT | AAT | ACA | 6220 |

```
Asn Lys Leu Leu Phe Ser Cys Ser Cys Lys Thr Ser His Thr Asn Thr
        2010                2015                2020

ATA GGT ACC ATG AAA GTT ACT CTA AAT AAA GAT GAA AAA GAA GAA GAA         6268
Ile Gly Thr Met Lys Val Thr Leu Asn Lys Asp Glu Lys Glu Glu Glu
2025                2030                2035                2040

GAT TTT AAA ACA GCT CAA GGT ATT AAA CAT AAT AAT GTA CAT TTA TGT         6316
Asp Phe Lys Thr Ala Gln Gly Ile Lys His Asn Asn Val His Leu Cys
                2045                2050                2055

AAT TTC TTT GAT AAT CCT GAA TTA ACA TTT GAT AAT AAT AAA ATA GTT         6364
Asn Phe Phe Asp Asn Pro Glu Leu Thr Phe Asp Asn Asn Lys Ile Val
            2060                2065                2070

TTA TGT AAA ATC GAT GCA GAA CTG TTC TCA GAA GTA ATT ATA CAA TTA         6412
Leu Cys Lys Ile Asp Ala Glu Leu Phe Ser Glu Val Ile Ile Gln Leu
        2075                2080                2085

CCA ATA TTT GGA ACA AAG AAT GTA GAA GAA GGA GTA CAA AAT GAA GAA         6460
Pro Ile Phe Gly Thr Lys Asn Val Glu Glu Gly Val Gln Asn Glu Glu
    2090                2095                2100

TAT AAA AAA TTT TCA TTA AAA CCA TCA TTA GTT TTT GAT GAT AAC AAT         6508
Tyr Lys Lys Phe Ser Leu Lys Pro Ser Leu Val Phe Asp Asp Asn Asn
2105                2110                2115                2120

AAT GAT ATT AAA GTT ATA GGA AAA GAA AAA AAT GAA GTA TCT ATT AGT         6556
Asn Asp Ile Lys Val Ile Gly Lys Glu Lys Asn Glu Val Ser Ile Ser
                2125                2130                2135

TTA GCT TTG AAA GGG GTT TAT GGA AAT CGA ATT TTT ACT TTT GAT AAA         6604
Leu Ala Leu Lys Gly Val Tyr Gly Asn Arg Ile Phe Thr Phe Asp Lys
            2140                2145                2150

AAT GGA AAA AAA GGA GAA GGA ATT AGT TTT TTT ATA CCT CCA ATA AAA         6652
Asn Gly Lys Lys Gly Glu Gly Ile Ser Phe Phe Ile Pro Pro Ile Lys
        2155                2160                2165

CAA GAT ACA GAT TTA AAA TTT ATA ATT AAT GAA ACA ATA GAT AAT TCA         6700
Gln Asp Thr Asp Leu Lys Phe Ile Ile Asn Glu Thr Ile Asp Asn Ser
    2170                2175                2180

AAT ATT AAA CAA AGA GGA TTA ATA TAT ATT TTT GTT AGG AAA AAT GTA         6748
Asn Ile Lys Gln Arg Gly Leu Ile Tyr Ile Phe Val Arg Lys Asn Val
2185                2190                2195                2200

TCA GAA AAT TCA TTT AAA TTA TGT GAT TTC ACA ACA GGT TCG ACT TCA         6796
Ser Glu Asn Ser Phe Lys Leu Cys Asp Phe Thr Thr Gly Ser Thr Ser
                2205                2210                2215

TTA ATG GAA TTA AAT AGT CAA GTA AAA GAA AAA AAG TGC ACT GTT AAA         6844
Leu Met Glu Leu Asn Ser Gln Val Lys Glu Lys Lys Cys Thr Val Lys
            2220                2225                2230

ATT AAA AAA GGA GAT ATT TTT GGA TTG AAA TGT CCT AAA GGT TTT GCT         6892
Ile Lys Lys Gly Asp Ile Phe Gly Leu Lys Cys Pro Lys Gly Phe Ala
        2235                2240                2245

ATA TTT CCA CAA GCA TGT TTT AGT AAT GTT TTA TTA GAA TAT TAT AAA         6940
Ile Phe Pro Gln Ala Cys Phe Ser Asn Val Leu Leu Glu Tyr Tyr Lys
    2250                2255                2260

AGT GAT TAT GAA GAT AGT GAA CAT ATT AAT TAT TAT ATT CAT AAA GAT         6988
Ser Asp Tyr Glu Asp Ser Glu His Ile Asn Tyr Tyr Ile His Lys Asp
2265                2270                2275                2280

AAA AAA TAT AAT TTA AAA CCT AAA GAT GTT ATT GAA TTA ATG GAT GAA         7036
Lys Lys Tyr Asn Leu Lys Pro Lys Asp Val Ile Glu Leu Met Asp Glu
                2285                2290                2295

AAT TTT AGA GAA TTA CAA AAT ATA CAA CAA TAT ACA GGA ATA TCA AAT         7084
Asn Phe Arg Glu Leu Gln Asn Ile Gln Gln Tyr Thr Gly Ile Ser Asn
            2300                2305                2310

ATT ACA GAT GTG TTA CAT TTC AAA AAT TTT AAT TTA GGT AAT CTA CCA         7132
Ile Thr Asp Val Leu His Phe Lys Asn Phe Asn Leu Gly Asn Leu Pro
        2315                2320                2325

TTA AAT TTT AAA AAT CAT TAT TCT ACA GCA TAT GCT AAA GTA CCA GAT         7180
```

```
                Leu  Asn  Phe  Lys  Asn  His  Tyr  Ser  Thr  Ala  Tyr  Ala  Lys  Val  Pro  Asp
                     2330                     2335                    2340

ACC  TTT  AAT  TCT  ATT  ATT  AAC  TTC  TCA  TGT  AAT  TGT  TAT  AAT  CCA  GAA                    7228
Thr  Phe  Asn  Ser  Ile  Ile  Asn  Phe  Ser  Cys  Asn  Cys  Tyr  Asn  Pro  Glu
2345                     2350                    2355                    2360

AAA  CAT  GTA  TAT  GGT  ACT  ATG  CAA  GTT  GAG  TCT  GAT  AAT  CGA  AAT  TTT                    7276
Lys  His  Val  Tyr  Gly  Thr  Met  Gln  Val  Glu  Ser  Asp  Asn  Arg  Asn  Phe
                    2365                    2370                    2375

GAT  AAT  ATT  AAA  AAA  AAT  GAA  AAT  GTT  ATA  AAA  AAT  TTC  CTT  TTA  CCT                    7324
Asp  Asn  Ile  Lys  Lys  Asn  Glu  Asn  Val  Ile  Lys  Asn  Phe  Leu  Leu  Pro
               2380                    2385                    2390

AAT  ATA  GAA  AAA  TAT  GCA  CTA  CTA  TTA  GAT  GAT  GAA  GAA  AGA  CAA  AAA                    7372
Asn  Ile  Glu  Lys  Tyr  Ala  Leu  Leu  Leu  Asp  Asp  Glu  Glu  Arg  Gln  Lys
          2395                    2400                    2405

AAA  ATA  AAA  CAA  CAA  CAA  GAA  GAA  GAA  CAA  CAA  GAA  CAA  ATA  TTA  AAA                    7420
Lys  Ile  Lys  Gln  Gln  Gln  Glu  Glu  Glu  Gln  Gln  Glu  Gln  Ile  Leu  Lys
     2410                    2415                    2420

GAT  CAA  GAT  GAT  AGA  TTA  AGC  AGA  CAT  GAT  GAT  TAT  AAT  AAA  AAT  CAT                    7468
Asp  Gln  Asp  Asp  Arg  Leu  Ser  Arg  His  Asp  Asp  Tyr  Asn  Lys  Asn  His
2425                     2430                    2435                    2440

ACA  TAT  ATA  CTA  TAT  GAT  TCA  AAT  GAA  CAT  ATA  TGT  GAT  TAT  GAA  AAA                    7516
Thr  Tyr  Ile  Leu  Tyr  Asp  Ser  Asn  Glu  His  Ile  Cys  Asp  Tyr  Glu  Lys
                    2445                    2450                    2455

AAT  GAA  TCA  CTC  ATA  TCA  ACA  TTA  CCT  AAT  GAT  ACA  AAA  AAA  ATA  CAA                    7564
Asn  Glu  Ser  Leu  Ile  Ser  Thr  Leu  Pro  Asn  Asp  Thr  Lys  Lys  Ile  Gln
               2460                    2465                    2470

AAA  AGT  ATC  TGT  AAA  ATT  AAT  GCA  AAA  GCA  TTA  GAT  GTT  GTT  ACA  ATT                    7612
Lys  Ser  Ile  Cys  Lys  Ile  Asn  Ala  Lys  Ala  Leu  Asp  Val  Val  Thr  Ile
          2475                    2480                    2485

AAA  TGT  CCT  CAT  ACA  AAA  AAT  TTT  ACG  CCT  AAA  GAT  TAT  TTT  CCT  AAT                    7660
Lys  Cys  Pro  His  Thr  Lys  Asn  Phe  Thr  Pro  Lys  Asp  Tyr  Phe  Pro  Asn
     2490                    2495                    2500

TCT  TCA  TTA  ATA  ACT  AAT  GAT  AAA  AAA  ATT  GTG  ATT  ACT  TTT  GAT  AAG                    7708
Ser  Ser  Leu  Ile  Thr  Asn  Asp  Lys  Lys  Ile  Val  Ile  Thr  Phe  Asp  Lys
2505                     2510                    2515                    2520

AAA  AAT  TTT  GTT  ACT  TAT  ATA  GAT  CCT  ACA  AAA  AAA  ACA  TTT  TCT  TTG                    7756
Lys  Asn  Phe  Val  Thr  Tyr  Ile  Asp  Pro  Thr  Lys  Lys  Thr  Phe  Ser  Leu
                    2525                    2530                    2535

AAA  GAT  ATA  TAT  ATA  CAA  AGT  TTT  TAT  GGT  GTT  TCT  CTT  GAT  CAT  CTT                    7804
Lys  Asp  Ile  Tyr  Ile  Gln  Ser  Phe  Tyr  Gly  Val  Ser  Leu  Asp  His  Leu
               2540                    2545                    2550

AAT  CAA  ATA  AAA  AAA  ATA  CAT  GAA  GAA  TGG  GAT  GAT  GTA  CAT  TTA  TTT                    7852
Asn  Gln  Ile  Lys  Lys  Ile  His  Glu  Glu  Trp  Asp  Asp  Val  His  Leu  Phe
          2555                    2560                    2565

TAT  CCT  CCT  CAT  AAT  GTA  TTA  CAT  AAT  GTT  GTA  CTT  AAT  AAT  CAT  ATA                    7900
Tyr  Pro  Pro  His  Asn  Val  Leu  His  Asn  Val  Val  Leu  Asn  Asn  His  Ile
     2570                    2575                    2580

GTC  AAC  TTA  TCA  TCT  GCA  TTA  GAA  GGA  GTC  TTA  TTT  ATG  AAA  TCA  AAA                    7948
Val  Asn  Leu  Ser  Ser  Ala  Leu  Glu  Gly  Val  Leu  Phe  Met  Lys  Ser  Lys
2585                     2590                    2595                    2600

GTT  ACT  GGA  GAT  GAA  ACA  GCT  ACA  AAA  AAA  AAC  ACT  ACA  CTA  CCA  ACT                    7996
Val  Thr  Gly  Asp  Glu  Thr  Ala  Thr  Lys  Lys  Asn  Thr  Thr  Leu  Pro  Thr
                    2605                    2610                    2615

GAT  GGT  GTA  TCA  AGT  ATT  TTA  ATT  CCA  CCA  TAT  GTA  AAG  GAA  GAT  ATA                    8044
Asp  Gly  Val  Ser  Ser  Ile  Leu  Ile  Pro  Pro  Tyr  Val  Lys  Glu  Asp  Ile
               2620                    2625                    2630

ACA  TTT  CAT  CTT  TTT  TGT  GGG  AAA  TCT  ACA  ACA  AAA  AAA  CCA  AAC  AAA                    8092
Thr  Phe  His  Leu  Phe  Cys  Gly  Lys  Ser  Thr  Thr  Lys  Lys  Pro  Asn  Lys
          2635                    2640                    2645

AAG  AAC  ACA  TCT  CTT  GCA  CTT  ATT  CAT  ATA  CAT  ATA  TCA  TCA  AAC  AGA                    8140
```

| | | | | | | | | | | | | | | | | |
|---|---|---|---|---|---|---|---|---|---|---|---|---|---|---|---|---|
| Lys | Asn | Thr | Ser | Leu | Ala | Leu | Ile | His | Ile | His | Ile | Ser | Ser | Asn | Arg | |
| | | | 2650 | | | | 2655 | | | | 2660 | | | | | |
| AAT | ATT | ATT | CAT | GGA | TGT | GAT | TTC | TTA | TAT | TTA | GAA | AAT | CAA | ACA | AAT | 8188 |
| Asn | Ile | Ile | His | Gly | Cys | Asp | Phe | Leu | Tyr | Leu | Glu | Asn | Gln | Thr | Asn | |
| 2665 | | | | | 2670 | | | | 2675 | | | | | 2680 | | |
| GAT | GCT | ATT | AGT | AAT | AAT | AAT | AAT | AAT | TCA | TAT | TCT | ATA | TTT | ACA | CAT | 8236 |
| Asp | Ala | Ile | Ser | Asn | Asn | Asn | Asn | Asn | Ser | Tyr | Ser | Ile | Phe | Thr | His | |
| | | | | 2685 | | | | | 2690 | | | | 2695 | | | |
| AAT | AAA | AAT | ACA | GAG | AAT | AAT | CTA | ATA | TGT | GAT | ATA | TCT | TTA | ATT | CCA | 8284 |
| Asn | Lys | Asn | Thr | Glu | Asn | Asn | Leu | Ile | Cys | Asp | Ile | Ser | Leu | Ile | Pro | |
| | | | 2700 | | | | | 2705 | | | | | 2710 | | | |
| AAA | ACT | GTT | ATA | GGA | ATT | AAA | TGT | CCT | AAT | AAA | AAA | TTA | AAT | CCA | CAA | 8332 |
| Lys | Thr | Val | Ile | Gly | Ile | Lys | Cys | Pro | Asn | Lys | Lys | Leu | Asn | Pro | Gln | |
| | | | 2715 | | | | 2720 | | | | | 2725 | | | | |
| ACA | TGT | TTT | GAT | GAA | GTG | TAT | TAT | GTT | AAA | CAA | GAA | GAT | GTA | CCT | TCG | 8380 |
| Thr | Cys | Phe | Asp | Glu | Val | Tyr | Tyr | Val | Lys | Gln | Glu | Asp | Val | Pro | Ser | |
| | | | | 2730 | | | | 2735 | | | | | 2740 | | | |
| AAA | ACT | ATA | ACA | GCT | GAT | AAA | TAT | AAT | ACA | TTT | AGT | AAA | GAC | AAA | ATA | 8428 |
| Lys | Thr | Ile | Thr | Ala | Asp | Lys | Tyr | Asn | Thr | Phe | Ser | Lys | Asp | Lys | Ile | |
| 2745 | | | | | 2750 | | | | 2755 | | | | | 2760 | | |
| GGA | AAT | ATA | TTA | AAA | AAT | GCA | ATC | TCT | ATT | AAT | AAT | CCA | GAT | GAA | AAG | 8476 |
| Gly | Asn | Ile | Leu | Lys | Asn | Ala | Ile | Ser | Ile | Asn | Asn | Pro | Asp | Glu | Lys | |
| | | | | 2765 | | | | | 2770 | | | | | 2775 | | |
| GAT | AAT | ACA | TAT | ACT | TAT | TTA | ATA | TTA | CCA | GAA | AAA | TTT | GAA | GAA | GAA | 8524 |
| Asp | Asn | Thr | Tyr | Thr | Tyr | Leu | Ile | Leu | Pro | Glu | Lys | Phe | Glu | Glu | Glu | |
| | | | | 2780 | | | | 2785 | | | | | 2790 | | | |
| TTA | ATC | GAT | ACC | AAA | AAA | GTT | TTA | GCT | TGT | ACA | TGT | GAT | AAT | AAA | TAT | 8572 |
| Leu | Ile | Asp | Thr | Lys | Lys | Val | Leu | Ala | Cys | Thr | Cys | Asp | Asn | Lys | Tyr | |
| | | | 2795 | | | | 2800 | | | | | 2805 | | | | |
| ATA | ATA | CAT | ATG | AAA | ATA | GAA | AAA | AGT | ACA | ATG | GAT | AAA | ATA | AAA | ATA | 8620 |
| Ile | Ile | His | Met | Lys | Ile | Glu | Lys | Ser | Thr | Met | Asp | Lys | Ile | Lys | Ile | |
| | | | 2810 | | | | | 2815 | | | | | 2820 | | | |
| GAT | GAA | AAA | AAA | ACA | ATT | GGT | AAA | GAT | ATA | TGT | AAA | TAT | GAT | GTT | ACT | 8668 |
| Asp | Glu | Lys | Lys | Thr | Ile | Gly | Lys | Asp | Ile | Cys | Lys | Tyr | Asp | Val | Thr | |
| 2825 | | | | | 2830 | | | | 2835 | | | | | | 2840 | |
| ACT | AAA | GTT | GCT | ACT | TGT | GAA | ATT | ATT | GAT | ACA | ATT | GAT | TCG | TCT | GTA | 8716 |
| Thr | Lys | Val | Ala | Thr | Cys | Glu | Ile | Ile | Asp | Thr | Ile | Asp | Ser | Ser | Val | |
| | | | | 2845 | | | | | 2850 | | | | | 2855 | | |
| TTA | AAA | GAA | CAT | CAT | ACA | GTA | CAT | TAT | TCT | ATT | ACA | TTA | TCA | AGA | TGG | 8764 |
| Leu | Lys | Glu | His | His | Thr | Val | His | Tyr | Ser | Ile | Thr | Leu | Ser | Arg | Trp | |
| | | | | 2860 | | | | 2865 | | | | | 2870 | | | |
| GAT | AAA | CTT | ATT | ATT | AAA | TAT | CCA | ACA | AAT | GAG | AAA | ACA | CAT | TTC | GAA | 8812 |
| Asp | Lys | Leu | Ile | Ile | Lys | Tyr | Pro | Thr | Asn | Glu | Lys | Thr | His | Phe | Glu | |
| | | | 2875 | | | | | 2880 | | | | | 2885 | | | |
| AAT | TTT | TTT | GTT | AAT | CCT | TTT | AAT | TTA | AAA | GAT | AAA | GTT | TTA | TAT | AAT | 8860 |
| Asn | Phe | Phe | Val | Asn | Pro | Phe | Asn | Leu | Lys | Asp | Lys | Val | Leu | Tyr | Asn | |
| | | | 2890 | | | | | 2895 | | | | | 2900 | | | |
| TAT | AAT | AAA | CCA | ATA | AAT | ATA | GAA | CAT | ATC | TTA | CCA | GGA | GCC | ATT | ACA | 8908 |
| Tyr | Asn | Lys | Pro | Ile | Asn | Ile | Glu | His | Ile | Leu | Pro | Gly | Ala | Ile | Thr | |
| 2905 | | | | | 2910 | | | | | 2915 | | | | | 2920 | |
| ACA | GAT | ATA | TAT | GAT | ACC | AGA | ACA | AAA | ATT | AAA | CAA | TAT | ATA | TTA | AGA | 8956 |
| Thr | Asp | Ile | Tyr | Asp | Thr | Arg | Thr | Lys | Ile | Lys | Gln | Tyr | Ile | Leu | Arg | |
| | | | | 2925 | | | | | 2930 | | | | | 2935 | | |
| ATT | CCA | CCA | TAT | GTA | CAT | AAA | GAT | ATA | CAT | TTC | TCA | TTA | GAA | TTT | AAC | 9004 |
| Ile | Pro | Pro | Tyr | Val | His | Lys | Asp | Ile | His | Phe | Ser | Leu | Glu | Phe | Asn | |
| | | | | 2940 | | | | | 2945 | | | | | 2950 | | |
| AAT | AGC | CTA | AGT | TTA | ACA | AAA | CAA | AAT | CAA | AAT | ATT | ATT | TAT | GGA | AAT | 9052 |
| Asn | Ser | Leu | Ser | Leu | Thr | Lys | Gln | Asn | Gln | Asn | Ile | Ile | Tyr | Gly | Asn | |
| | | | | 2955 | | | | | 2960 | | | | | 2965 | | |
| GTA | GCC | AAA | ATT | TTT | ATT | CAT | ATA | AAT | CAA | GGA | TAT | AAA | GAA | ATT | CAT | 9100 |

|     |     |     |     |     |     |     |     |     |     |     |     |     |     |     |     |
|---|---|---|---|---|---|---|---|---|---|---|---|---|---|---|---|
| Val | Ala | Lys | Ile | Phe | Ile | His | Ile | Asn | Gln | Gly | Tyr | Lys | Glu | Ile | His |
|     | 2970 |     |     |     | 2975 |     |     |     |     | 2980 |     |     |     |     |     |

GGA TGT GAT TTC ACA GGA AAA TAT TCC CAT TTA TTT ACA TAT TCA AAA    9148
Gly Cys Asp Phe Thr Gly Lys Tyr Ser His Leu Phe Thr Tyr Ser Lys
2985            2990                2995                    3000

AAA CCT TTA CCA AAT GAT GAT GAT ATA TGT AAT GTA ACT ATA GGT AAT    9196
Lys Pro Leu Pro Asn Asp Asp Asp Ile Cys Asn Val Thr Ile Gly Asn
                3005                3010                3015

AAT ACA TTC TCA GGT TTT GCA TGC TTA AGC CAT TTT GAA TTA AAA CCA    9244
Asn Thr Phe Ser Gly Phe Ala Cys Leu Ser His Phe Glu Leu Lys Pro
            3020                3025                3030

AAT AAC TGC TTC TCA TCT GTT TAT GAT TAT AAT GAA GCC AAT AAA GTT    9292
Asn Asn Cys Phe Ser Ser Val Tyr Asp Tyr Asn Glu Ala Asn Lys Val
        3035                3040                3045

AAA AAA TTA TTC GAT CTA TCC ACA AAA GTA GAA TTA GAC CAT ATC AAA    9340
Lys Lys Leu Phe Asp Leu Ser Thr Lys Val Glu Leu Asp His Ile Lys
    3050                3055                3060

CAA AAT ACT TCA GGA TAT ACA CTA TCA TAT ATT ATT TTT AAT AAA GAA    9388
Gln Asn Thr Ser Gly Tyr Thr Leu Ser Tyr Ile Ile Phe Asn Lys Glu
3065            3070                3075                    3080

TCC ACA AAA CTT AAA TTC TCA TGT ACA TGC TCA TCC AAC TAT TCA AAT    9436
Ser Thr Lys Leu Lys Phe Ser Cys Thr Cys Ser Ser Asn Tyr Ser Asn
                3085                3090                3095

TAT ACT ATA CGA ATC ACA TTT GAT CCT AAT TAT ATA ATC CCA GAA CCT    9484
Tyr Thr Ile Arg Ile Thr Phe Asp Pro Asn Tyr Ile Ile Pro Glu Pro
            3100                3105                3110

CAA TCA AGA GCC ATC ATT AAA TAT GTA GAT CTG CAA GAT AAA AAT TTT    9532
Gln Ser Arg Ala Ile Ile Lys Tyr Val Asp Leu Gln Asp Lys Asn Phe
        3115                3120                3125

GCA AAA TAC TTG AGA AAG CTT TAAATCGTAA ATAATTAATC AAACATATAT       9583
Ala Lys Tyr Leu Arg Lys Leu
    3130            3135

ATAATCAAAA GGATAATATA TTAGAACACA CATATATATG TAAAAAAAAA AAA         9636

( 2 ) INFORMATION FOR SEQ ID NO:2:

( i ) SEQUENCE CHARACTERISTICS:
        ( A ) LENGTH: 3135 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Lys Lys Ile Ile Thr Leu Lys Asn Leu Phe Leu Ile Ile Leu Val
1               5                   10                  15

Tyr Ile Phe Ser Glu Lys Lys Asp Leu Arg Cys Asn Val Ile Lys Gly
            20                  25                  30

Asn Asn Ile Lys Asp Asp Glu Asp Lys Arg Phe His Leu Phe Tyr Tyr
        35                  40                  45

Ser His Asn Leu Phe Lys Thr Pro Glu Thr Lys Glu Lys Asn Lys
    50                  55                  60

Lys Glu Cys Phe Tyr Lys Asn Gly Gly Ile Tyr Asn Leu Ser Lys Glu
65              70                  75                  80

Ile Arg Met Arg Lys Asp Thr Ser Val Lys Ile Lys Gln Arg Thr Cys
            85                  90                  95

Pro Phe His Lys Glu Gly Ser Ser Phe Glu Met Gly Ser Lys Asn Ile
        100                 105                 110

Thr Cys Phe Tyr Pro Ile Val Gly Lys Lys Glu Arg Lys Thr Leu Asp
    115                 120                 125

-continued

| Thr | Ile | Ile | Ile | Lys | Lys | Asn | Val | Thr | Asn | Asp | His | Val | Val | Ser | Ser |
| | 130 | | | | 135 | | | | 140 | | | | | | |
| Asp | Met | His | Ser | Asn | Val | Gln | Glu | Lys | Asn | Met | Ile | Leu | Ile | Arg | Asn |
| 145 | | | | | 150 | | | | 155 | | | | | | 160 |
| Ile | Asp | Lys | Glu | Asn | Lys | Asn | Asp | Ile | Gln | Asn | Val | Glu | Glu | Lys | Ile |
| | | | | 165 | | | | | 170 | | | | | 175 | |
| Gln | Arg | Asp | Thr | Tyr | Glu | Asn | Lys | Asp | Tyr | Glu | Ser | Asp | Asp | Thr | Leu |
| | | | 180 | | | | | 185 | | | | | 190 | | |
| Ile | Glu | Trp | Phe | Asp | Asp | Asn | Thr | Asn | Glu | Glu | Asn | Phe | Leu | Leu | Thr |
| | | 195 | | | | | 200 | | | | | 205 | | | |
| Phe | Leu | Lys | Arg | Cys | Leu | Met | Lys | Ile | Phe | Ser | Ser | Pro | Lys | Arg | Lys |
| | 210 | | | | | 215 | | | | | 220 | | | | |
| Lys | Thr | Val | Val | Gln | Lys | Lys | His | Lys | Ser | Asn | Phe | Phe | Ile | Asn | Ser |
| 225 | | | | | 230 | | | | | 235 | | | | | 240 |
| Ser | Leu | Lys | Tyr | Ile | Tyr | Met | Tyr | Leu | Thr | Pro | Ser | Asp | Ser | Phe | Asn |
| | | | | 245 | | | | | 250 | | | | | 255 | |
| Leu | Val | Arg | Arg | Asn | Arg | Asn | Leu | Asp | Glu | Glu | Asp | Met | Ser | Pro | Arg |
| | | | 260 | | | | | 265 | | | | | 270 | | |
| Asp | Asn | Phe | Val | Ile | Asp | Asp | Glu | Glu | Glu | Glu | Glu | Glu | Glu | Glu | Glu |
| | | 275 | | | | | 280 | | | | | 285 | | | |
| Glu | Glu | Glu | Glu | Glu | Glu | Glu | Glu | Glu | Glu | Glu | Glu | Glu | Glu | Glu | Glu |
| | 290 | | | | | 295 | | | | | 300 | | | | |
| Tyr | Asp | Asp | Tyr | Val | Tyr | Glu | Glu | Ser | Gly | Asp | Glu | Thr | Glu | Glu | Gln |
| 305 | | | | | 310 | | | | | 315 | | | | | 320 |
| Leu | Gln | Glu | Glu | His | Gln | Glu | Glu | Val | Gly | Ala | Glu | Ser | Ser | Glu | Glu |
| | | | | 325 | | | | | 330 | | | | | 335 | |
| Ser | Phe | Asn | Asp | Glu | Asp | Glu | Asp | Ser | Val | Glu | Ala | Arg | Asp | Gly | Asp |
| | | | 340 | | | | | 345 | | | | | 350 | | |
| Met | Ile | Arg | Val | Asp | Glu | Tyr | Tyr | Glu | Asp | Gln | Asp | Gly | Asp | Thr | Tyr |
| | | 355 | | | | | 360 | | | | | 365 | | | |
| Asp | Ser | Thr | Ile | Lys | Asn | Glu | Asp | Val | Asp | Glu | Glu | Val | Gly | Glu | Glu |
| | 370 | | | | | 375 | | | | | 380 | | | | |
| Val | Gly | Glu | Glu | Val | Gly | Glu | Glu | Val | Gly | Glu | Glu | Val | Gly | Glu | Glu |
| 385 | | | | | 390 | | | | | 395 | | | | | 400 |
| Val | Gly | Glu | Glu | Val | Gly | Glu | Glu | Val | Gly | Glu | Glu | Val | Gly | Glu | Glu |
| | | | | 405 | | | | | 410 | | | | | 415 | |
| Glu | Gly | Glu | Glu | Val | Gly | Glu | Gly | Val | Gly | Glu | Glu | Val | Gly | Glu | Glu |
| | | | 420 | | | | | 425 | | | | | 430 | | |
| Glu | Gly | Glu | Glu | Val | Gly | Glu | Glu | Gly | Glu | Tyr | Val | Asp | Glu | Lys |
| | | 435 | | | | | 440 | | | | | 445 | | | |
| Glu | Arg | Gln | Gly | Glu | Ile | Tyr | Pro | Phe | Gly | Asp | Glu | Glu | Glu | Lys | Asp |
| | 450 | | | | | 455 | | | | | 460 | | | | |
| Glu | Gly | Gly | Glu | Ser | Phe | Thr | Tyr | Glu | Lys | Ser | Glu | Val | Asp | Lys | Thr |
| 465 | | | | | 470 | | | | | 475 | | | | | 480 |
| Asp | Leu | Phe | Lys | Phe | Ile | Glu | Gly | Gly | Glu | Gly | Asp | Asp | Val | Tyr | Lys |
| | | | | 485 | | | | | 490 | | | | | 495 | |
| Val | Asp | Gly | Ser | Lys | Val | Leu | Leu | Asp | Asp | Thr | Ile | Ser | Arg | Val |
| | | | 500 | | | | | 505 | | | | | 510 | | |
| Ser | Lys | Lys | His | Thr | Ala | Arg | Asp | Gly | Glu | Tyr | Gly | Glu | Tyr | Gly | Glu |
| | | 515 | | | | | 520 | | | | | 525 | | | |
| Ala | Val | Glu | Asp | Gly | Glu | Asn | Val | Ile | Lys | Ile | Ile | Arg | Ser | Val | Leu |
| | 530 | | | | | 535 | | | | | 540 | | | | |
| Gln | Ser | Gly | Ala | Leu | Pro | Ser | Val | Gly | Val | Asp | Glu | Leu | Asp | Lys | Ile |

-continued

```
545                    550                    555                    560
Asp Leu Ser Tyr Glu Thr Thr Glu Ser Gly Asp Thr Ala Val Ser Glu
                565                    570                    575
Asp Ser Tyr Asp Lys Tyr Ala Ser Asn Asn Thr Asn Lys Glu Tyr Val
                580                    585                    590
Cys Asp Phe Thr Asp Gln Leu Lys Pro Thr Glu Ser Gly Pro Lys Val
                595                    600                    605
Lys Lys Cys Glu Val Lys Val Asn Glu Pro Leu Ile Lys Val Lys Ile
        610                    615                    620
Ile Cys Pro Leu Lys Gly Ser Val Glu Lys Leu Tyr Asp Asn Ile Glu
625                    630                    635                    640
Tyr Val Pro Lys Lys Ser Pro Tyr Val Val Leu Thr Lys Glu Glu Thr
                645                    650                    655
Lys Leu Lys Glu Lys Leu Leu Ser Lys Leu Ile Tyr Gly Leu Leu Ile
                660                    665                    670
Ser Pro Thr Val Asn Glu Lys Glu Asn Asn Phe Lys Glu Gly Val Ile
            675                    680                    685
Glu Phe Thr Leu Pro Pro Val Val His Lys Ala Thr Val Phe Tyr Phe
        690                    695                    700
Ile Cys Asp Asn Ser Lys Thr Glu Asp Asp Asn Lys Lys Gly Asn Arg
705                    710                    715                    720
Gly Ile Val Glu Val Tyr Val Glu Pro Tyr Gly Asn Lys Ile Asn Gly
                725                    730                    735
Cys Ala Phe Leu Asp Glu Asp Glu Glu Glu Lys Tyr Gly Asn Gln
                740                    745                    750
Ile Glu Glu Asp Glu His Asn Glu Lys Ile Lys Met Lys Thr Phe Phe
            755                    760                    765
Thr Gln Asn Ile Tyr Lys Lys Asn Asn Ile Tyr Pro Cys Tyr Met Lys
        770                    775                    780
Leu Tyr Ser Gly Asp Ile Gly Gly Ile Leu Phe Pro Lys Asn Ile Lys
785                    790                    795                    800
Ser Thr Thr Cys Phe Glu Glu Met Ile Pro Tyr Asn Lys Glu Ile Lys
                805                    810                    815
Trp Asn Lys Glu Asn Lys Ser Leu Gly Asn Leu Val Asn Asn Ser Val
                820                    825                    830
Val Tyr Asn Lys Glu Met Asn Ala Lys Tyr Phe Asn Val Gln Tyr Val
        835                    840                    845
His Ile Pro Thr Ser Tyr Lys Asp Thr Leu Asn Leu Phe Cys Ser Ile
    850                    855                    860
Ile Leu Lys Glu Glu Glu Ser Asn Leu Ile Ser Thr Ser Tyr Leu Val
865                    870                    875                    880
Tyr Val Ser Ile Asn Glu Glu Leu Asn Phe Ser Leu Phe Asp Phe Tyr
                885                    890                    895
Glu Ser Phe Val Pro Ile Lys Lys Thr Ile Gln Val Ala Gln Lys Asn
            900                    905                    910
Val Asn Asn Lys Glu His Asp Tyr Thr Cys Asp Phe Thr Asp Lys Leu
        915                    920                    925
Asp Lys Thr Val Pro Ser Thr Ala Asn Gly Lys Lys Leu Phe Ile Cys
    930                    935                    940
Arg Lys His Leu Lys Glu Phe Asp Thr Phe Thr Leu Lys Cys Asn Val
945                    950                    955                    960
Asn Lys Thr Gln Tyr Pro Asn Ile Glu Ile Phe Pro Lys Thr Leu Lys
                965                    970                    975
```

```
Asp Lys Lys Glu Val Leu Lys Leu Asp Leu Asp Ile Gln Tyr Gln Met
            980                 985                 990
Phe Ser Lys Phe Phe Lys Phe Asn Thr Gln Asn Ala Lys Tyr Leu Asn
        995                 1000                1005
Leu Tyr Pro Tyr Tyr Leu Ile Phe Pro Phe Asn His Ile Gly Lys Lys
        1010                1015                1020
Glu Leu Lys Asn Asn Pro Thr Tyr Lys Asn His Lys Asp Val Lys Tyr
1025                1030                1035                1040
Phe Glu Gln Ser Ser Val Leu Ser Pro Leu Ser Ser Ala Asp Ser Leu
                1045                1050                1055
Gly Lys Leu Leu Asn Phe Leu Asp Thr Gln Glu Thr Val Cys Leu Thr
            1060                1065                1070
Glu Lys Ile Arg Tyr Leu Asn Leu Ser Ile Asn Glu Leu Gly Ser Asp
            1075                1080                1085
Asn Asn Thr Phe Ser Val Thr Phe Gln Val Pro Pro Tyr Ile Asp Ile
            1090                1095                1100
Lys Glu Pro Phe Tyr Phe Met Phe Gly Cys Asn Asn Asn Lys Gly Glu
1105                1110                1115                1120
Gly Asn Ile Gly Ile Val Glu Leu Leu Ile Ser Lys Gln Glu Glu Lys
            1125                1130                1135
Ile Lys Gly Cys Asn Phe His Glu Ser Lys Leu Asp Tyr Phe Asn Glu
            1140                1145                1150
Asn Ile Ser Ser Asp Thr His Glu Cys Thr Leu His Ala Tyr Glu Asn
            1155                1160                1165
Asp Ile Ile Gly Phe Asn Cys Leu Glu Thr Thr His Pro Asn Glu Val
            1170                1175                1180
Glu Val Glu Val Glu Asp Ala Glu Ile Tyr Leu Gln Pro Glu Asn Cys
1185                1190                1195                1200
Phe Asn Asn Val Tyr Lys Gly Leu Asn Ser Val Asp Ile Thr Thr Ile
                1205                1210                1215
Leu Lys Asn Ala Gln Thr Tyr Asn Ile Asn Asn Lys Lys Thr Pro Thr
            1220                1225                1230
Phe Leu Lys Ile Pro Pro Tyr Asn Leu Leu Glu Asp Val Glu Ile Ser
            1235                1240                1245
Cys Gln Cys Thr Ile Lys Gln Val Val Lys Lys Ile Lys Val Ile Ile
            1250                1255                1260
Thr Lys Asn Asp Thr Val Leu Leu Lys Arg Glu Val Gln Ser Glu Ser
1265                1270                1275                1280
Thr Leu Asp Asp Lys Ile Tyr Lys Cys Glu His Glu Asn Phe Ile Asn
                1285                1290                1295
Pro Arg Val Asn Lys Thr Phe Asp Glu Asn Val Glu Tyr Thr Cys Asn
            1300                1305                1310
Ile Lys Ile Glu Asn Phe Phe Asn Tyr Ile Gln Ile Phe Cys Pro Ala
            1315                1320                1325
Lys Asp Leu Gly Ile Tyr Lys Asn Ile Gln Met Tyr Tyr Asp Ile Val
            1330                1335                1340
Lys Pro Thr Arg Val Pro Gln Phe Lys Lys Phe Asn Asn Glu Glu Leu
1345                1350                1355                1360
His Lys Leu Ile Pro Asn Ser Glu Met Leu His Lys Thr Lys Glu Met
                1365                1370                1375
Leu Ile Leu Tyr Asn Glu Glu Lys Val Asp Leu Leu His Phe Tyr Val
            1380                1385                1390
Phe Leu Pro Ile Tyr Ile Lys Asp Ile Tyr Glu Phe Asn Ile Val Cys
            1395                1400                1405
```

```
Asp Asn Ser Lys Thr Met Trp Lys Asn Gln Leu Gly Gly Lys Val Ile
    1410            1415                1420

Tyr His Ile Thr Val Ser Lys Arg Glu Gln Lys Val Lys Gly Cys Ser
1425            1430            1435                        1440

Phe Asp Asn Glu His Ala His Met Phe Ser Tyr Asn Lys Thr Asn Val
                1445            1450                    1455

Lys Asn Cys Ile Ile Asp Ala Lys Pro Lys Asp Leu Ile Gly Phe Val
            1460            1465                1470

Cys Pro Ser Gly Thr Leu Lys Leu Thr Asn Cys Phe Lys Asp Ala Ile
            1475            1480            1485

Val His Thr Asn Leu Thr Asn Ile Asn Gly Ile Leu Tyr Leu Lys Asn
        1490            1495            1500

Asn Leu Ala Asn Phe Thr Tyr Lys His Gln Phe Asn Tyr Met Glu Ile
1505            1510            1515                        1520

Pro Ala Leu Met Asp Asn Asp Ile Ser Phe Lys Cys Ile Cys Val Asp
                1525            1530            1535

Leu Lys Lys Lys Lys Tyr Asn Val Lys Ser Pro Leu Gly Pro Lys Val
            1540            1545            1550

Leu Arg Ala Leu Tyr Lys Lys Leu Asn Ile Lys Phe Asp Asn Tyr Val
        1555            1560            1565

Thr Gly Thr Asp Gln Asn Lys Tyr Leu Met Thr Tyr Met Asp Leu His
    1570            1575            1580

Leu Ser His Lys Arg Asn Tyr Leu Lys Glu Leu Phe His Asp Leu Gly
1585            1590            1595                        1600

Lys Lys Lys Pro Ala Asp Thr Asp Ala Asn Pro Glu Ser Ile Ile Glu
            1605            1610            1615

Ser Leu Ser Ile Asn Glu Ser Asn Glu Ser Gly Pro Phe Pro Thr Gly
            1620            1625            1630

Asp Val Asp Ala Glu His Leu Ile Leu Glu Gly Tyr Asp Thr Trp Glu
        1635            1640            1645

Ser Leu Tyr Asp Glu Gln Leu Glu Glu Val Ile Tyr Asn Asp Ile Glu
    1650            1655            1660

Ser Leu Glu Leu Lys Asp Ile Glu Gln Tyr Val Leu Gln Val Asn Leu
1665            1670            1675                        1680

Lys Ala Pro Lys Leu Met Met Ser Ala Gln Ile His Asn Asn Arg His
            1685            1690            1695

Val Cys Asp Phe Ser Lys Asn Asn Leu Ile Val Pro Glu Ser Leu Lys
            1700            1705            1710

Lys Lys Glu Glu Leu Gly Gly Asn Pro Val Asn Ile His Cys Tyr Ala
        1715            1720            1725

Leu Leu Lys Pro Leu Asp Thr Leu Tyr Val Lys Cys Pro Thr Ser Lys
    1730            1735            1740

Asp Asn Tyr Glu Ala Ala Lys Val Asn Ile Ser Glu Asn Asp Asn Glu
1745            1750            1755                        1760

Tyr Glu Leu Gln Val Ile Ser Leu Ile Glu Lys Arg Phe His Asn Phe
            1765            1770            1775

Glu Thr Leu Glu Ser Lys Lys Pro Gly Asn Gly Asp Val Val Val His
            1780            1785            1790

Asn Gly Val Val Asp Thr Gly Pro Val Leu Asp Asn Ser Thr Phe Glu
        1795            1800            1805

Lys Tyr Phe Lys Asn Ile Lys Ile Lys Pro Asp Lys Phe Phe Glu Lys
    1810            1815            1820

Val Ile Asn Glu Tyr Asp Asp Thr Glu Glu Glu Lys Asp Leu Glu Ser
```

-continued

```
                1825                    1830                    1835                    1840
Ile  Leu  Pro  Gly  Ala  Ile  Val  Ser  Pro  Met  Lys  Val  Leu  Lys  Lys  Lys
                    1845                    1850                    1855
Asp  Pro  Phe  Thr  Ser  Tyr  Ala  Ala  Phe  Val  Val  Pro  Pro  Ile  Val  Pro
                    1860                    1865                    1870
Lys  Asp  Leu  His  Phe  Lys  Val  Glu  Cys  Asn  Asn  Thr  Glu  Tyr  Lys  Asp
                    1875                    1880                    1885
Glu  Asn  Gln  Tyr  Ile  Ser  Gly  Tyr  Asn  Gly  Ile  Ile  His  Ile  Asp  Ile
                    1890                    1895                    1900
Ser  Asn  Ser  Asn  Arg  Lys  Ile  Asn  Gly  Cys  Asp  Phe  Ser  Thr  Asn  Asn
1905                    1910                    1915                    1920
Ser  Ser  Ile  Leu  Thr  Ser  Ser  Val  Lys  Leu  Val  Asn  Gly  Glu  Thr  Lys
                    1925                    1930                    1935
Asn  Cys  Glu  Ile  Asn  Ile  Asn  Asn  Asn  Glu  Val  Phe  Gly  Ile  Ile  Cys
                    1940                    1945                    1950
Asp  Asn  Glu  Thr  Asn  Leu  Asp  Pro  Glu  Lys  Cys  Phe  His  Glu  Ile  Tyr
                    1955                    1960                    1965
Ser  Lys  Asp  Asn  Lys  Thr  Val  Lys  Lys  Phe  Arg  Glu  Val  Ile  Pro  Asn
                    1970                    1975                    1980
Ile  Asp  Ile  Phe  Ser  Leu  His  Asn  Ser  Asn  Lys  Lys  Lys  Val  Ala  Tyr
1985                    1990                    1995                    2000
Ala  Lys  Val  Pro  Leu  Asp  Tyr  Ile  Asn  Lys  Leu  Leu  Phe  Ser  Cys  Ser
                    2005                    2010                    2015
Cys  Lys  Thr  Ser  His  Thr  Asn  Thr  Ile  Gly  Thr  Met  Lys  Val  Thr  Leu
                    2020                    2025                    2030
Asn  Lys  Asp  Glu  Lys  Glu  Glu  Glu  Asp  Phe  Lys  Thr  Ala  Gln  Gly  Ile
                    2035                    2040                    2045
Lys  His  Asn  Asn  Val  His  Leu  Cys  Asn  Phe  Phe  Asp  Asn  Pro  Glu  Leu
                    2050                    2055                    2060
Thr  Phe  Asp  Asn  Asn  Lys  Ile  Val  Leu  Cys  Lys  Ile  Asp  Ala  Glu  Leu
2065                    2070                    2075                    2080
Phe  Ser  Glu  Val  Ile  Ile  Gln  Leu  Pro  Ile  Phe  Gly  Thr  Lys  Asn  Val
                    2085                    2090                    2095
Glu  Glu  Gly  Val  Gln  Asn  Glu  Glu  Tyr  Lys  Lys  Phe  Ser  Leu  Lys  Pro
                    2100                    2105                    2110
Ser  Leu  Val  Phe  Asp  Asp  Asn  Asn  Asn  Asp  Ile  Lys  Val  Ile  Gly  Lys
                    2115                    2120                    2125
Glu  Lys  Asn  Glu  Val  Ser  Ile  Ser  Leu  Ala  Leu  Lys  Gly  Val  Tyr  Gly
                    2130                    2135                    2140
Asn  Arg  Ile  Phe  Thr  Phe  Asp  Lys  Asn  Gly  Lys  Lys  Gly  Glu  Gly  Ile
2145                    2150                    2155                    2160
Ser  Phe  Phe  Ile  Pro  Pro  Ile  Lys  Gln  Asp  Thr  Asp  Leu  Lys  Phe  Ile
                    2165                    2170                    2175
Ile  Asn  Glu  Thr  Ile  Asp  Asn  Ser  Asn  Ile  Lys  Gln  Arg  Gly  Leu  Ile
                    2180                    2185                    2190
Tyr  Ile  Phe  Val  Arg  Lys  Asn  Val  Ser  Glu  Asn  Ser  Phe  Lys  Leu  Cys
                    2195                    2200                    2205
Asp  Phe  Thr  Thr  Gly  Ser  Thr  Ser  Leu  Met  Glu  Leu  Asn  Ser  Gln  Val
                    2210                    2215                    2220
Lys  Glu  Lys  Lys  Cys  Thr  Val  Lys  Ile  Lys  Lys  Gly  Asp  Ile  Phe  Gly
2225                    2230                    2235                    2240
Leu  Lys  Cys  Pro  Lys  Gly  Phe  Ala  Ile  Phe  Pro  Gln  Ala  Cys  Phe  Ser
                    2245                    2250                    2255
```

```
Asn Val Leu Leu Glu Tyr Tyr Lys Ser Asp Tyr Glu Asp Ser Glu His
       2260                2265                2270
Ile Asn Tyr Tyr Ile His Lys Asp Lys Lys Tyr Asn Leu Lys Pro Lys
       2275                2280                2285
Asp Val Ile Glu Leu Met Asp Glu Asn Phe Arg Glu Leu Gln Asn Ile
       2290                2295                2300
Gln Gln Tyr Thr Gly Ile Ser Asn Ile Thr Asp Val Leu His Phe Lys
2305                2310                2315                2320
Asn Phe Asn Leu Gly Asn Leu Pro Leu Asn Phe Lys Asn His Tyr Ser
            2325                2330                2335
Thr Ala Tyr Ala Lys Val Pro Asp Thr Phe Asn Ser Ile Ile Asn Phe
            2340                2345                2350
Ser Cys Asn Cys Tyr Asn Pro Glu Lys His Val Tyr Gly Thr Met Gln
            2355                2360                2365
Val Glu Ser Asp Asn Arg Asn Phe Asp Asn Ile Lys Lys Asn Glu Asn
       2370                2375                2380
Val Ile Lys Asn Phe Leu Leu Pro Asn Ile Glu Lys Tyr Ala Leu Leu
2385                2390                2395                2400
Leu Asp Asp Glu Glu Arg Gln Lys Lys Ile Lys Gln Gln Gln Glu Glu
            2405                2410                2415
Glu Gln Gln Glu Gln Ile Leu Lys Asp Gln Asp Asp Arg Leu Ser Arg
            2420                2425                2430
His Asp Asp Tyr Asn Lys Asn His Thr Tyr Ile Leu Tyr Asp Ser Asn
            2435                2440                2445
Glu His Ile Cys Asp Tyr Glu Lys Asn Glu Ser Leu Ile Ser Thr Leu
            2450                2455                2460
Pro Asn Asp Thr Lys Lys Ile Gln Lys Ser Ile Cys Lys Ile Asn Ala
2465                2470                2475                2480
Lys Ala Leu Asp Val Val Thr Ile Lys Cys Pro His Thr Lys Asn Phe
            2485                2490                2495
Thr Pro Lys Asp Tyr Phe Pro Asn Ser Ser Leu Ile Thr Asn Asp Lys
            2500                2505                2510
Lys Ile Val Ile Thr Phe Asp Lys Lys Asn Phe Val Thr Tyr Ile Asp
            2515                2520                2525
Pro Thr Lys Lys Thr Phe Ser Leu Lys Asp Ile Tyr Ile Gln Ser Phe
            2530                2535                2540
Tyr Gly Val Ser Leu Asp His Leu Asn Gln Ile Lys Lys Ile His Glu
2545                2550                2555                2560
Glu Trp Asp Asp Val His Leu Phe Tyr Pro Pro His Asn Val Leu His
            2565                2570                2575
Asn Val Val Leu Asn Asn His Ile Val Asn Leu Ser Ser Ala Leu Glu
            2580                2585                2590
Gly Val Leu Phe Met Lys Ser Lys Val Thr Gly Asp Glu Thr Ala Thr
            2595                2600                2605
Lys Lys Asn Thr Thr Leu Pro Thr Asp Gly Val Ser Ser Ile Leu Ile
       2610                2615                2620
Pro Pro Tyr Val Lys Glu Asp Ile Thr Phe His Leu Phe Cys Gly Lys
2625                2630                2635                2640
Ser Thr Thr Lys Lys Pro Asn Lys Lys Asn Thr Ser Leu Ala Leu Ile
            2645                2650                2655
His Ile His Ile Ser Ser Asn Arg Asn Ile Ile His Gly Cys Asp Phe
            2660                2665                2670
Leu Tyr Leu Glu Asn Gln Thr Asn Asp Ala Ile Ser Asn Asn Asn Asn
            2675                2680                2685
```

```
Asn  Ser  Tyr  Ser  Ile  Phe  Thr  His  Asn  Lys  Asn  Thr  Glu  Asn  Asn  Leu
     2690                2695                2700

Ile  Cys  Asp  Ile  Ser  Leu  Ile  Pro  Lys  Thr  Val  Ile  Gly  Ile  Lys  Cys
2705                2710                2715                          2720

Pro  Asn  Lys  Lys  Leu  Asn  Pro  Gln  Thr  Cys  Phe  Asp  Glu  Val  Tyr  Tyr
               2725                2730                          2735

Val  Lys  Gln  Glu  Asp  Val  Pro  Ser  Lys  Thr  Ile  Thr  Ala  Asp  Lys  Tyr
          2740                     2745                     2750

Asn  Thr  Phe  Ser  Lys  Asp  Lys  Ile  Gly  Asn  Ile  Leu  Lys  Asn  Ala  Ile
          2755                2760                     2765

Ser  Ile  Asn  Asn  Pro  Asp  Glu  Lys  Asp  Asn  Thr  Tyr  Thr  Tyr  Leu  Ile
2770                     2775                     2780

Leu  Pro  Glu  Lys  Phe  Glu  Glu  Leu  Ile  Asp  Thr  Lys  Lys  Val  Leu
2785                     2790                2795                     2800

Ala  Cys  Thr  Cys  Asp  Asn  Lys  Tyr  Ile  Ile  His  Met  Lys  Ile  Glu  Lys
                    2805                2810                     2815

Ser  Thr  Met  Asp  Lys  Ile  Lys  Ile  Asp  Glu  Lys  Lys  Thr  Ile  Gly  Lys
               2820                2825                     2830

Asp  Ile  Cys  Lys  Tyr  Asp  Val  Thr  Thr  Lys  Val  Ala  Thr  Cys  Glu  Ile
     2835                     2840                     2845

Ile  Asp  Thr  Ile  Asp  Ser  Ser  Val  Leu  Lys  Glu  His  His  Thr  Val  His
2850                          2855                     2860

Tyr  Ser  Ile  Thr  Leu  Ser  Arg  Trp  Asp  Lys  Leu  Ile  Ile  Lys  Tyr  Pro
2865                2870                2875                          2880

Thr  Asn  Glu  Lys  Thr  His  Phe  Glu  Asn  Phe  Phe  Val  Asn  Pro  Phe  Asn
                    2885                2890                     2895

Leu  Lys  Asp  Lys  Val  Leu  Tyr  Asn  Tyr  Asn  Lys  Pro  Ile  Asn  Ile  Glu
          2900                2905                     2910

His  Ile  Leu  Pro  Gly  Ala  Ile  Thr  Thr  Asp  Ile  Tyr  Asp  Thr  Arg  Thr
     2915                     2920                     2925

Lys  Ile  Lys  Gln  Tyr  Ile  Leu  Arg  Ile  Pro  Pro  Tyr  Val  His  Lys  Asp
     2930                     2935                2940

Ile  His  Phe  Ser  Leu  Glu  Phe  Asn  Asn  Ser  Leu  Ser  Leu  Thr  Lys  Gln
2945                     2950                2955                     2960

Asn  Gln  Asn  Ile  Ile  Tyr  Gly  Asn  Val  Ala  Lys  Ile  Phe  Ile  His  Ile
               2965                2970                     2975

Asn  Gln  Gly  Tyr  Lys  Glu  Ile  His  Gly  Cys  Asp  Phe  Thr  Gly  Lys  Tyr
          2980                2985                     2990

Ser  His  Leu  Phe  Thr  Tyr  Ser  Lys  Lys  Pro  Leu  Pro  Asn  Asp  Asp  Asp
     2995                3000                     3005

Ile  Cys  Asn  Val  Thr  Ile  Gly  Asn  Asn  Thr  Phe  Ser  Gly  Phe  Ala  Cys
3010                     3015                     3020

Leu  Ser  His  Phe  Glu  Leu  Lys  Pro  Asn  Asn  Cys  Phe  Ser  Ser  Val  Tyr
3025                3030                     3035                     3040

Asp  Tyr  Asn  Glu  Ala  Asn  Lys  Val  Lys  Lys  Leu  Phe  Asp  Leu  Ser  Thr
               3045                3050                     3055

Lys  Val  Glu  Leu  Asp  His  Ile  Lys  Gln  Asn  Thr  Ser  Gly  Tyr  Thr  Leu
          3060                3065                     3070

Ser  Tyr  Ile  Ile  Phe  Asn  Lys  Glu  Ser  Thr  Lys  Leu  Lys  Phe  Ser  Cys
     3075                3080                     3085

Thr  Cys  Ser  Ser  Asn  Tyr  Ser  Asn  Tyr  Thr  Ile  Arg  Ile  Thr  Phe  Asp
3090                     3095                3100

Pro  Asn  Tyr  Ile  Ile  Pro  Glu  Pro  Gln  Ser  Arg  Ala  Ile  Ile  Lys  Tyr
```

| 3105 | 3110 | 3115 | 3120 |

Val Asp Leu Gln Asp Lys Asn Phe Ala Lys Tyr Leu Arg Lys Leu
              3125              3130           3135

( 2 ) INFORMATION FOR SEQ ID NO:3:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:3:

Glu Glu Val Gly
 1

( 2 ) INFORMATION FOR SEQ ID NO:4:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 6
  ( D ) OTHER INFORMATION: /product="OTHER"
   / note="Xaa =Glu or Gly"

( i x ) FEATURE:
  ( A ) NAME/KEY: Modified-site
  ( B ) LOCATION: 7
  ( D ) OTHER INFORMATION: /product="OTHER"
   / note="Xaa =Glu or Val"

( x i ) SEQUENCE DESCRIPTION: SEQ ID NO:4:

Glu Glu Val Gly Glu Xaa Xaa Gly
 1               5